(12) United States Patent
LeMahieu et al.

(10) Patent No.: US 6,585,713 B1
(45) Date of Patent: Jul. 1, 2003

(54) ABSORBENT ARTICLE PROVIDING A DYNAMIC FIT

(75) Inventors: Lynn Kirkpatrick LeMahieu, Hortonville, WI (US); David Arthur Fell, Neenah, WI (US); Sarah Jane Marie Freiburger, Kaukauna, WI (US); Marianne Keevill Leick, Appleton, WI (US); Michael Tod Morman, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/749,133

(22) Filed: Nov. 14, 1996

(51) Int. Cl.$^7$ .................................. A61F 13/15
(52) U.S. Cl. ...................... 604/392; 604/391
(58) Field of Search ................. 604/385.1, 385.2, 604/392, 393, 394, 397, 385.01, 385.101, 385.14, 385.24, 385.29, 385.3, 386, 396, 391

(56) References Cited

U.S. PATENT DOCUMENTS

| | | | |
|---|---|---|---|
| 1,494,044 A | 5/1924 | Ward et al. | |
| 2,516,951 A | 8/1950 | Brink | |
| 2,548,162 A | 4/1951 | Karels | |
| 2,566,139 A | 8/1951 | Ostrovsky et al. | |
| 3,110,312 A | 11/1963 | Wirth | |
| 3,227,160 A | 1/1966 | Younger | |
| 3,955,575 A | 5/1976 | Okuda | |
| 4,205,679 A | 6/1980 | Repke et al. | |
| 4,316,508 A | 2/1982 | Bolick | |
| 4,388,075 A | 6/1983 | Mesek et al. | |
| 4,425,128 A | 1/1984 | Motomura | |
| 4,606,964 A | 8/1986 | Wideman | |
| 4,610,680 A | 9/1986 | LaFleur | |
| 4,652,487 A | 3/1987 | Morman | |
| 4,655,760 A | 4/1987 | Morman et al. | |
| 4,657,802 A | 4/1987 | Morman | |
| 4,663,220 A | 5/1987 | Wisneski et al. | |
| 4,699,823 A | 10/1987 | Kellenberger et al. | |
| 4,710,187 A * | 12/1987 | Boland et al. | 604/385.2 |
| 4,720,415 A | 1/1988 | Vander Wielen et al. | |
| 4,770,656 A | 9/1988 | Proxmire et al. | 604/393 |
| 4,781,966 A | 11/1988 | Taylor | |
| 4,789,699 A | 12/1988 | Kieffer et al. | |
| 4,808,176 A | 2/1989 | Kielpikowski | 604/385.2 |
| 4,834,738 A | 5/1989 | Kielpikowski et al. | 604/385.2 |
| 4,846,825 A | 7/1989 | Enloe et al. | 604/385.1 |
| 4,847,134 A | 7/1989 | Fahrenkrug et al. | |
| 4,880,424 A | 11/1989 | Rautenberg | 604/396 |
| 4,886,512 A | 12/1989 | Damico et al. | 604/385.2 |

(List continued on next page.)

FOREIGN PATENT DOCUMENTS

| | | |
|---|---|---|
| EP | 0 217 032 A2 | 4/1987 |
| EP | 0 345 664 A1 | 12/1989 |
| EP | 0 601 610 A1 | 6/1994 |
| EP | 0 648 482 A3 | 4/1995 |
| EP | 0 705 584 A1 | 4/1996 |
| WO | WO 95/14453 | 6/1995 |
| WO | WO 95/16421 | 6/1995 |
| WO | WO 95/22951 | 8/1995 |
| WO | WO 96/14039 | 5/1996 |

OTHER PUBLICATIONS

American Society for Testing and Material (ASTM) Designation: E96—93, "Standard Test Methods for Water Vapor Transmission of Materials," pp. 701–708, published 1993.

Primary Examiner—Weilun Lo
Assistant Examiner—Jamisue A. Webb
(74) Attorney, Agent, or Firm—Thomas M. Gage; Patricia A. Charlier; Scott A. Baum

(57) ABSTRACT

An absorbent article includes a garment having opposite waist regions separated by a crotch region. At least one of the waist regions includes an expansion panel adapted to elongate in a direction substantially perpendicular to the longitudinal axis of the garment. The absorbent article also includes a pair of elastomeric strap members that are adapted to attach to the waist regions.

31 Claims, 8 Drawing Sheets

U.S. PATENT DOCUMENTS

| | | | |
|---|---|---|---|
| 4,909,802 A | 3/1990 | Ahr et al. ................. 604/385.1 |
| 4,932,950 A * | 6/1990 | Johnson ..................... 604/390 |
| 4,936,840 A | 6/1990 | Proxmire ................. 604/385.2 |
| 4,937,887 A | 7/1990 | Schreiner ........................ 2/402 |
| 4,938,754 A | 7/1990 | Mesek ..................... 604/385.2 |
| 4,938,757 A | 7/1990 | Van Gompel et al. ...... 604/396 |
| 4,940,464 A | 7/1990 | Van Gompel et al. ...... 604/396 |
| 4,964,860 A | 10/1990 | Gipson et al. .............. 604/391 |
| 4,965,122 A | 10/1990 | Morman |
| 5,026,364 A | 6/1991 | Robertson |
| 5,114,781 A | 5/1992 | Morman |
| 5,116,662 A | 5/1992 | Morman |
| 5,147,343 A | 9/1992 | Kellenberger ............... 604/368 |
| 5,196,000 A | 3/1993 | Clear et al. .............. 604/385.2 |
| 5,197,960 A * | 3/1993 | Nomura et al. ............. 604/392 |
| 5,226,992 A | 7/1993 | Morman ..................... 156/62.4 |
| 5,227,107 A | 7/1993 | Dickenson et al. ......... 264/113 |
| 5,304,162 A | 4/1994 | Kuen .......................... 604/391 |
| 5,332,613 A | 7/1994 | Taylor et al. |
| 5,336,545 A | 8/1994 | Morman |
| 5,374,262 A | 12/1994 | Keuhn, Jr. et al. .......... 604/391 |
| 5,376,198 A | 12/1994 | Fahrenkrug et al. |
| 5,383,867 A | 1/1995 | Klinger ..................... 604/385.1 |
| 5,386,595 A | 2/1995 | Kuen et al. ..................... 2/400 |
| 5,409,476 A * | 4/1995 | Coates .................. 604/385.14 |
| 5,411,498 A | 5/1995 | Fahrenkrug et al. ..... 604/385.2 |
| 5,496,298 A | 3/1996 | Kuepper et al. ............. 604/389 |
| 5,514,470 A | 5/1996 | Haffner et al. |
| 5,545,158 A | 8/1996 | Jessup ..................... 604/385.2 |
| 5,569,232 A | 10/1996 | Roe et al. ................. 604/385.2 |
| 5,669,901 A * | 9/1997 | LaFortune et al. .......... 604/392 |
| 5,695,488 A * | 12/1997 | Sosalla ....................... 604/392 |
| 5,722,968 A * | 3/1998 | Datta et al. ................. 604/392 |
| 5,776,123 A * | 7/1998 | Goerg et al. ............. 604/385.2 |

* cited by examiner

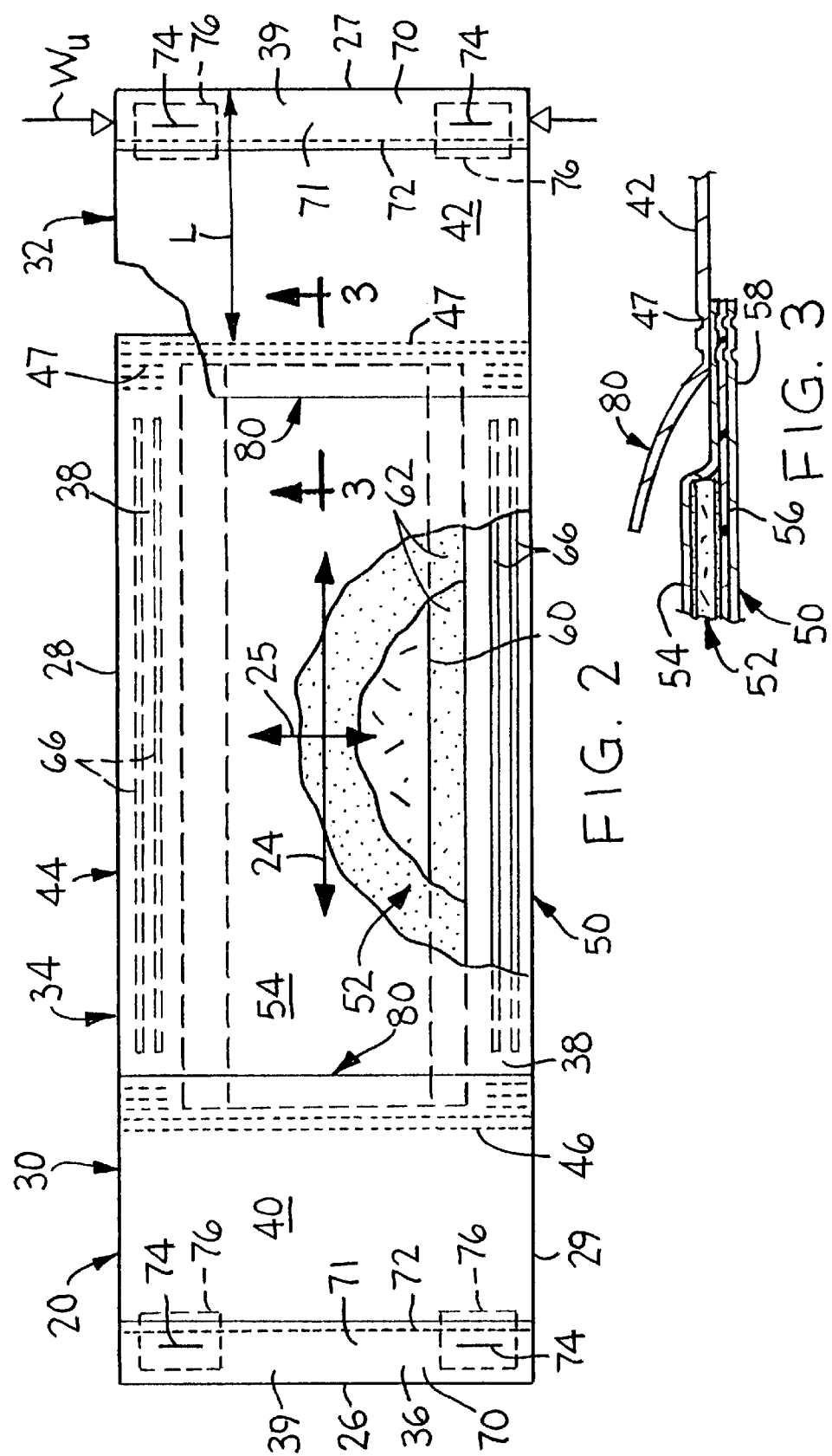

ABSORBENT ARTICLE PROVIDING A DYNAMIC FIT

BACKGROUND OF THE INVENTION

The present invention relates to garments and suspension systems. More particularly, the invention pertains to an absorbent article including an absorbent garment and a multi-component suspension and attachment system for the garment.

Undergarments for adult incontinence are generally characterized by the use of a pair of elastic straps in combination with a generally rectangular garment. Other than the incorporation of generally longitudinally-extending elastic members, these garments are commonly formed of non-stretchable materials. The elastic straps releasably attach to the front and back portions of the garment and stretch in use in an attempt to hold the garment up and about the wearer and in proper position to receive and contain urine. One drawback of such undergarments is that movements of the wearer may significantly impact the position and comfort of the garment. The garment may assume a position that is not advantageous for receiving liquid, and may even create gaps adjacent the wearer.

Therefore, what is lacking and needed in the art is an improved garment and strap suspension and attachment system that enhances garment fit and wearer comfort.

SUMMARY OF THE INVENTION

In response to the discussed deficiencies in the prior art, a new absorbent article has been developed. In one embodiment, an absorbent article includes a garment having a longitudinal axis, a first waist region, a second waist region, and a crotch region intermediate and interconnecting the first and second waist regions. The first waist region is adapted to elongate in a direction substantially perpendicular to the longitudinal axis. The absorbent article also includes a pair of separate elastomeric trap members, each having opposite ends adapted to attach to the waist regions.

In this embodiment, the first waist region is adapted to elongate in the transverse direction of the absorbent article. During use, the strap members tend to function in conjunction with the first waist region to maintain the garment up and about the wearer without sagging. In particular, the strap members tend to pull upward and outward on the waist regions of the garment. The outward or transverse component of this force tends to elongate the first waist region substantially perpendicular to the longitudinal axis of the garment.

One beneficial result is that the elastomeric properties of the strap members cause the first waist region to elongate to a larger surface area. The amount of transverse elongation increases from a relatively small amount adjacent the crotch region to its maximum near the longitudinal end edge of the first waist region. Consequently, a greater portion of the wearer's lower abdomen or buttocks is thereby covered by the first waist region. The elongatable first waist region may be positioned toward either the front or the back of the wearer, or alternatively, both the first and the second waist regions may be adapted to elongate in the transverse direction of the absorbent article.

The first waist region suitably comprises an elongatable material. In one particular embodiment, for instance, the first waist region may comprise a material that is adapted to elongate up to a maximum elongation without tending to retract to its unstretched state. In other embodiments, however, the first waist region comprises an elastomeric material to facilitate proper positioning of the garment. The combination of the elastomeric strap members and the elastomeric first waist region working in series causes the absorbent portion of the garment to undergo less shifting during use. Also, the combination of the elastomeric strap members and-the elastomeric first waist region provides improved comfort by distributing the elastic forces about a greater portion of the circumference of the wearer.

An absorbent article according to another embodiment includes a garment having a longitudinal axis, a first waist region, a second waist region, and a crotch region intermediate and interconnecting the first and second waist regions. The garment includes an expansion panel disposed in both the first and second waist regions and adapted to elongate in a direction substantially perpendicular to the longitudinal axis. An absorbent structure of the garment is disposed on the expansion panel in the crotch region. A pair of separate elastomeric strap members that each have opposite ends that are adapted to attach to the waist regions.

This embodiment allows for transverse extensibility in both waist regions through the use of a single expansion panel that extends substantially the full length of the absorbent article. To contain moisture in the storage assembly, the expansion panel may comprise a liquid impermeable material, or the absorbent article may comprise a separate liquid impermeable moisture barrier bonded to the expansion panel. The crotch region of the garment may, in one embodiment, be coated with a non-elastic polymer so this portion of the garment does not stretch. Alternatively, the absorbent article may comprise nonextensible zones between the crotch region and the waist regions to isolate the extension and/or elastic properties of each region.

Numerous features and advantages of the present invention will appear from the following description. In the description, reference is made to the accompanying drawings which illustrate the preferred embodiments of the invention. Such embodiments do not represent the full scope of the invention. Reference should therefore be made to the claims herein for interpreting the full scope of the invention.

BRIEF DESCRIPTION OF THE DRAWINGS

FIG. 2 representatively shows a plan view of a garment of the absorbent article shown in FIG. 1, taken from the bodyside of the absorbent article in a longitudinally stretched and laid flat condition and with portions broken away for purposes of illustration.

FIG. 3 representatively shows an enlarged section view taken generally from the plane of the line 3—3 in FIG. 2.

DETAILED DESCRIPTION OF THE PREFERRED EMBODIMENTS

Figure 1:
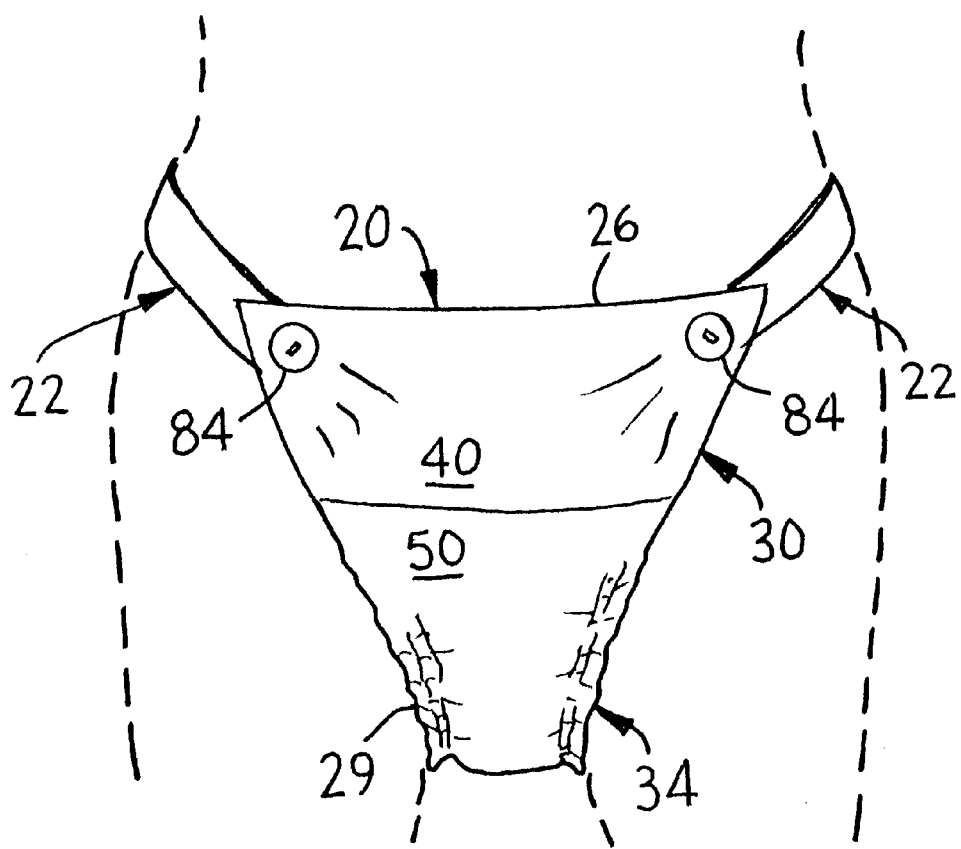
FIG. 1 representatively shows a front view of an absorbent article according to one embodiment of the present invention, in a typical use condition.

With reference to FIGS. 1 and 2, an absorbent article formed according to the invention is shown for purposes of illustration as a disposable undergarment 20 for adult incontinence which is maintained in position about a wearer by a pair of strap members 22. As used herein, the term "disposable" includes being disposed of after use and not intended to be washed and reused. The absorbent article is illustrated in a position representing use of the product in FIG. 1, and the undergarment 20 is illustrated alone and in a laid flat condition with the leg elastics stretched out in FIG. 2. The invention may also be embodied in other types of garments, such as other disposable absorbent articles, for example diapers, reusable absorbent articles, other personal care or health care garments, or the like.

The illustrated undergarment 20 defines a longitudinal axis or center line represented by arrow 24 and a transverse axis or center line represented by arrow 25 (FIG. 2). The undergarment 20 has a first or front longitudinal end edge 26, an opposite second or back longitudinal end edge 27, and first and second longitudinal side edges 28 and 29 that extend between the longitudinal end edges. The undergarment 20 includes a first or front waist region 30, a second or back waist region 32, and an intermediate, crotch region 34 positioned between and interconnecting the front and back waist regions. The outer edges of the undergarment 20 define a periphery 36 in which the longitudinally extending side margins are designated 38 and the laterally extending end margins are designated 39.

The end edges 26 and 27 and side edges 28 and 29 are desirably straight forming a rectangular shape when the garment 20 is laid flat and longitudinally stretched, but optionally, may be curvilinear and contoured.

The waist regions 30 and 32 of the undergarment 20 comprise first and second expansion panels 40 and 42. As explained in greater detail below, the expansion panels 40 and 42 are adapted to elongate during use in a direction that is substantially perpendicular to the longitudinal axis 24 of the undergarment 20. By elongating substantially perpendicular to the longitudinal axis 24, the expansion panels provide greater coverage over the abdomen and buttocks of the wearer. In particular embodiments, the expansion panels 40 and 42 comprise elastomeric materials that function in combination with the elastomeric strap members 22 so that the liquid storage portion of the garment 20 undergoes less shifting during use. Comfort is also enhanced because the elastic forces of the undergarment 20 are distributed about a greater portion of the circumference of the wearer. Correspondingly, the undergarment 20 conforms better to the body of the wearer so that fewer gaps are formed between the undergarment and the body.

Comparison of the shape of the undergarment 20 in FIGS. 1 and 2 illustrates an important feature of the invention. In FIG. 2 the garment 20 is longitudinally stretched so that the leg elastics 66 are elongated and the garment can lay flat. In this condition, the garment 20 has generally straight end edges 26 and 27 and side edges 28 and 29. Accordingly, the garment 20 has a generally uniform width over the full length of the garment. In contrast, however, when the garment 20 is longitudinally and transversely stretched such as during use the garment has an hourglass or dog bone shape as illustrated in FIG. 1. The width of the waist regions 30 and 32 is actually greater during use than in the longitudinally stretched flat condition shown in FIG. 2 because the expansion panels 40 and 42 elongate in order to balance the retraction forces provided by the strap members 22. The crotch region 34 may be formed or treated to be substantially nonextensible in the transverse direction 25 so that its width remains the same before and during use, although it looks somewhat narrower in FIG. 1 because it is compressed between the legs of the wearer.

The undergarment 20 may include an expansion panel in only one waist region or an expansion panel in both waist regions 30 and 32. In the latter case, the elastomeric materials used to construct the expansion panels 40 and 42 may have the same or different elastomeric properties. In the latter case, the expansion panels 40 and 42 may be constructed with different expansion and/or retraction properties to enhance fit. For example, the expansion panel designed to be positioned toward the back of the wearer could be adapted to expand to a greater extent than the other expansion panel in order to provide greater buttock coverage.

The crotch region 34 of the undergarment 20 comprises a storage assembly 44 (FIG. 2) that is adapted to take in and retain liquids, such as urine. The storage assembly 44 is disposed between and interconnects the expansion panels 40 and 42. The terms "disposed," "disposed on," "disposed with," "disposed at," "disposed near" and variations thereof are intended to mean that one element can be integral with another element, or that one element can be a separate structure bonded to or placed with or placed near another element. Thus, the storage assembly 44 is spaced longitudinally inward from the end edges 26 and 27 and is separated from the end edges by the expansion panels 40 and 42.

The front waist region 30 is contiguous with the front end edge 26 and extends longitudinally inward therefrom toward the transverse center line 25. The back waist region 32 is contiguous with the back end edge 27 and extends longitudinally inward therefrom toward the transverse center line 25. For purposes of the present invention, the front and back waist regions 30 and 32 are considered to terminate at respective bond regions 46 and 47. These bond regions 46 and 47 represent locations at which the expansion panels 40 and 42 are bonded to the storage assembly 44. As used herein, the term "bonded" refers to the joining, adhering, connecting, attaching, or the like, of two elements. Two elements will be considered to be bonded together when they are bonded directly to one another or indirectly to one another, such as when each is directly bonded to intermediate elements.

In the embodiment illustrated in FIGS. 1 and 2, therefore, the first expansion panel 40, the second expansion panel 42 and the storage assembly 44 are separate structures that are bonded together at the bond regions 46 and 47. As used in the present specification, the term "separate" refers to two or more distinct elements rather than a single unitary element or various portions of a single unitary element. A wide variety of bonds may be suitable for joining these structures together, including ultrasonic bonds, thermal bonds, adhesive bonds, or the like.

The waist regions 30 and 32 comprise those upper portions of undergarment 20 which, when worn, wholly or partially cover or encircle the waist or mid-lower torso of the wearer. The intermediate, crotch region 34 comprises that portion of undergarment 20 which, when worn, is positioned between the legs of the wearer at the perineum and covers the lower torso of the wearer. Thus, the crotch region 34 is the area where insults of urine typically occur in the undergarment or other absorbent article.

With additional reference to FIG. 3, the storage assembly 44 includes a substantially liquid impermeable moisture barrier 50, an absorbent structure 52 disposed on the moisture barrier, and a substantially liquid permeable bodyside liner 54 bonded to the moisture barrier to sandwich the absorbent structure therebetween. As illustrated, the moisture barrier 50 and bodyside liner 54 are coterminous and longer and wider than the absorbent structure 52 so that the peripheries of the moisture barrier and bodyside liner may be bonded together using ultrasonic bonds, thermal bonds, adhesives, or other suitable means. The periphery of the moisture barrier 50, the bodyside liner 54, or the peripheries of both, desirably form the side margins 38 of the undergarment 20 and include the bond regions 46 and 47 for attachment of the expansion panels 40 and 42. The absorbent structure 52 may also be bonded to the moisture barrier 50 and/or the bodyside liner 54 using ultrasonic bonds, thermal bonds, adhesives, or other suitable means.

The moisture barrier 50 desirably comprises a material that is formed or treated to be liquid impermeable. Alternatively, the moisture barrier 50 may comprise a liquid permeable material and other suitable means may be provided to impede liquid movement away from the absorbent structure, such as a liquid impermeable layer (not shown) associated with the absorbent structure 52. The moisture barrier 50 may also be gas permeable, that is "breathable," such that gases encountered during use of the absorbent garment are able to pass through the material under ordinary use conditions, over either all or part of its surface area.

The moisture barrier 50 may comprise a single layer of material or a laminate of two or more separate layers of material. Suitable moisture barrier materials include films, wovens, nonwovens, laminates of films, wovens, and/or nonwovens, or the like. For example, the moisture barrier 50 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 50 is a polyethylene film that has a nominal thickness of about 0.025 millimeter and a systematic matte embossed pattern, and that has been corona treated on both sides. As best shown in FIG. 3, the illustrated moisture barrier material comprises an adhesive or thermal laminate comprising a cast or blown film 56 formed of polypropylene, polyethylene or the like, and a spunbond web 58 formed of polypropylene and polyethylene bicomponent fibers in a 50/50 side-by-side configuration.

The absorbent structure 52 comprises materials adapted to absorb and retain liquid waste. The absorbent structure 52 may comprise various absorbent materials, such as an airformed batt of cellulosic fibers such as wood pulp fluff or a coform material composed of a mixture of cellulosic fibers and synthetic polymer fibers. Polymer fibers may be incorporated, for example, in the manner described in U.S. Pat. No. 5,227,107 issued Jul. 13, 1993, to Dickenson et al. The absorbent structure 52 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 1987 to Kellenberger et al. and U.S. Pat. No. 5,147,343 issued Sept. 15, 1992 to Kellenberger, which are incorporated herein by reference. High-absorbency materials are available from various commercial vendors, such as Dow Chemical Company, Hoechst Celanese Corporation, and Allied Colloids, Inc.

The absorbent structure 52 may also include tissue, acquisition, and/or distribution layers to help maintain the integrity of fibrous absorbents or transport liquids (not shown). The illustrated absorbent structure 52 comprises an absorbent batt 60 sandwiched between two tissue layers 62 (FIG. 2). The general shape of the absorbent structure 52 may correspond to the shape of the storage assembly 44 or assume a different shape. In one alternative embodiment, the longitudinal ends of the absorbent structure 52 are coterminous with the longitudinal ends of the moisture barrier 50 and the bodyside liner 54.

The bodyside liner 54 is formed of a liquid permeable material so that liquid waste, and possibly semi-solid waste as well, can pass through the liner and be absorbed by the absorbent structure 52. Suitable bodyside liners 54 may comprise a nonwoven web or sheet of wet strength tissue paper, an apertured film, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 54 may be treated with a surfactant to aid in liquid transfer. In a particular embodiment of the invention, the liner 54 comprises a nonwoven, spunbond polypropylene fabric composed of about 2.8–3.2 denier fibers formed into a web having a basis weight of about 22 gsm and density of about 0.06 gm/cc. The fabric is surface treated with about 0.28 weight percent of a surfactant commercially available from Union Carbide Chemicals and Plastics Company, Inc., of Danbury, Conn., U.S.A. under the trade designation Triton X-102.

The term "fabric" is used herein to refer to all of the woven, knitted and nonwoven fibrous webs. The term "nonwoven web" means a web of material which is formed without the aid of a textile weaving or knitting process. Nonwoven webs have been formed from many processes such as for example, meltblowing processes, spunbonding processes, coforming, and bonded carded web processes. The basis weight of nonwoven fabrics is usually expressed in ounces of material per square yard (osy) or grams per square meter (gsm) and the fiber diameters useful are usually expressed in microns.

Desirably although not necessarily, the storage assembly 44 also includes leg elastic members 66 (FIG. 2) to draw and hold the side margins of the undergarment 20 against the legs of the wearer and form a seal therewith. The elongated leg elastic members 66 are longitudinally orientated in each side margin, extending toward the front and back end edges 26 and 27. The leg elastic members 66 are positioned in the illustrated embodiment between the moisture barrier 50 and the bodyside liner 54. Using ultrasonic bonds, adhesives, thermal bonds, or other suitable means, the leg elastic members 66 are attached in a stretched condition to the moisture barrier 50, the bodyside liner 54, or both, in either a straight or a curved shape. Alternatively, the leg elastic members 66 may be attached in a relaxed state to a gathered portion of the moisture barrier 50, the bodyside liner 54, or both.

The leg elastic members 66 may be formed of a dry-spun coalesced multifilament spandex elastomeric thread sold under the trade name LYCRA® and available from E. I. Du Pont de Nemours and Company. Alternately, the elastic members may be formed of other typical elastics utilized in the undergarment-making art, such as a thin ribbon of natural rubber, wet-spun spandex materials, a stretch bonded laminate material comprising a prestretched elastic meltblown inner layer sandwiched between and bonded to a pair of spunbond polypropylene nonwoven webs, or the like. Other suitable elastic gathering means are disclosed in U.S. Pat. No. 4,938,754 to Mesek and U.S. Pat. No. 4,388,075 to Mesek et al.

The expansion panels 40 and 42 are adapted to enable the waist regions 30 and 32 to elongate in the transverse direction 25 during use. More specifically, the elongation of the strap members 22 when donning the undergarment 20 provides a retraction force acting on the expansion panels 40 and 42 and directed at an angle relative to the longitudinal axis 24 of the undergarment. The effective width of the expansion panels 40 and 42 is caused to be increased by the transverse component of this retraction force, so that the expansion panels assume a roughly trapezoidal shape. The increased body coverage afforded by the expansion panels during use provides for greater comfort and feeling of security.

The expansion panels 40 and 42 are suitably formed of an elongatable material that is adapted to extend in response to an applied force. Thus, in one embodiment the expansion panels 40 and 42 are elongatable but do not totally recover upon removal of the applied force. Suitable elongatable materials possess a maximum elongation, that is a "stretch-to-stop" property, so that the expansion panels do not elongate to the point at which the attachment and suspension system can no longer maintain sufficient tension to hold the garment on the wearer. The terms "extension," "extend" and "extended" refer to the change in length of a material due to stretching, expressed in units of length. The term "force" includes a physical influence exerted by one body on another which produces acceleration of bodies that are free to move and deformation of bodies that are not free to move. The term "elongation" as used herein refers to the change in length of a material due to elongation, that is the elongated length minus the original length, divided by the original length of the material, multiplied by 100 and expressed in percent.

More desirably, the expansion panels 40 and 42 may be formed of an elastic or elastomeric material so that the extension and extension recovery properties of the expansion panels and the strap members 22 work in combination to enhance the fit of the undergarment 20. The terms "elastic," "elasticized" and "elasticity" are used herein to mean that property of a material by virtue of which it tends to recover its original size and shape after removal of a force causing a deformation. The term "elastomeric" as used herein refers to a material or composite which can be elongated by at least 60 percent of its relaxed length and which will recover, upon release of the applied force, at least 55 percent of its elongation.

As used herein the term "recover" refers to a contraction of a stretched material upon termination of a force following stretching of the material by application of the force. For example, if a material having a relaxed, unextended length of one (1) inch is elongated 20 percent by stretching to a length of one and two-tenths (1.2) inch, the material would have an extended length that is 120 percent of its unextended length. If this exemplary stretched material contracted, that is recovered to a length of one and one-tenth (1.1) inch after release of the stretching force, the material would have recovered 50 percent (0.1 inch) of its elongation.

As noted previously, the expansion panels 40 and 42 are desirably adapted to elongate in a direction that is substantially perpendicular to the longitudinal axis 24 of the undergarment 20. Thus, the expansion panels 40 and 42 may be formed of a "CD stretch" material that is adapted to elongate in a direction that is perpendicular to the longitudinal axis 24. The term "substantially perpendicular" as used herein refers to a material adapted to elongate in a direction that forms an angle with the longitudinal axis 24 of between about 70 and 90 degrees, and more particularly between about 80 and 90 degrees, and desirably about 90 degrees, such as 90 degrees. Applicants presently hypothesize that significant amounts of elasticity in the longitudinal direction, for example elongations of greater than about 10 percent in the longitudinal direction 24 under typical use conditions, may diminish the ability of the undergarment 20 to resist sagging when fully loaded with urine.

To enhance comfort of the undergarment 20, the expansion panels 40 and 42 may be formed of a "breathable" material. For example, the expansion panels 40 and 42 suitably have a Water Vapor Transmission Rate (WVTR) of at least about 1,000 grams per square meter per 24 hours ($gm/m^2/24$ hrs). One suitable procedure for determining the WVTR of a material is the Water Vapor Transmission Rate Test set forth in the Test Procedures section below.

Additionally, the expansion panels 40 and 42 may beneficially have a relatively low ability to wick liquids. In particular embodiments, for example, the expansion panels 40 and 42 have a liquid wicking rate of less than about 3 centimeters per 30 minutes. The Liquid Wicking Test which is included in the Test Procedures section below is a suitable procedure for determining the liquid wicking properties of the 30 expansion panels 40 and 42.

Examples of materials suitable for constructing the expansion panels 40 and 42 include elongatable materials, elastic materials, or elastomeric materials, such as polymer films, woven fabrics, knits, nonwoven fabrics or the like, as well as combinations thereof. In particular aspects of the invention, the expansion panels 40 and 42 can be composed of a stretch-bonded-laminate (SBL) material, a neck-bonded-laminate (NBL) material, a reversibly necked nonwoven material, an elastomeric film, and elastomeric foam material, elastic threads or the like. For example, suitable meltblown elastomeric fibrous webs for forming expansion panels 40 and 42 are described in U.S. Pat. No. 4,663,220 issued May 5, 1987 to T. Wisneski et al., the disclosure of which is hereby incorporated by reference. Examples of composite fabrics comprising at least one layer of nonwoven textile fabric secured to a fibrous elastic layer are described in European Patent Application EP No. 0 217 032 A2 published on Apr. 8, 1987 with the inventors listed as J. Taylor et al., the disclosure of which is hereby incorporated by reference. Examples of NBL materials are described in U.S. Pat. No. 5,226,992 issued Jul. 13, 1993 to Morman; U.S. Pat. No. 5,336,545 issued Aug. 9, 1994 to Morman; and U.S. Pat. No. 5,514,470 issued May 7, 1996 to Haffner et al.; the disclosures of which are incorporated herein by reference.

As described previously, the expansion panels 40 and 42 may be formed of a material capable of stretching in one direction or less desirably capable of stretching in multiple directions. One suitable one-directional stretch material is disclosed in U.S. Pat. No. 4,720,415 issued Jan. 19, 1988 to Vander Wielen et al., which is incorporated herein by reference. The one-directional stretch material may comprise a composite material including at least one gatherable web bonded to at least one elongated elastic web. The elastic web may be an elastic film or nonwoven fibrous elastic webs such as meltblown elastomeric fibrous webs. In one embodiment, the expansion panels comprise a stretch bonded laminate formed of a prestretched elastic meltblown inner layer sandwiched between and attached to a pair of spunbond polypropylene nonwoven webs having a basis weight of about 13.6 gsm (0.4 oz/yd$^2$). Suitable elastic materials can be purchased from the Shell Chemical Company of Houston, Tex. under the trade name KRATON. Other suitable one-directional stretch materials are disclosed in U.S. Pat. No. 4,965,112 issued Oct. 23, 1990 to Morman; 4,606,964 issued Aug. 19, 1986 to Wideman; and 4,657,802 issued Apr. 14, 1987 to Morman.

Two-directional stretch materials that could be used for the expansion panels 40 and 42 are disclosed in U.S. Pat. No. 5,114,781 issued May 19, 1992 and 5,116,662 issued May 26, 1992 to Morman, which are incorporated herein by reference. A two-directional stretch material may comprise a composite material including a neckable material and an elastic sheet, which may be formed by meltblowing or extrusion. Neckable materials are those which may be constricted in at least one dimension by applying a tensioning force in a direction perpendicular to the desired direction of neck-down, and may include a spunbonded, meltblown or bonded carded web. The tensioned, necked neckable material may be joined to the elongated elastic sheet at spaced locations arranged in a nonlinear configuration. Another two-directional stretch composite material may comprise one or more layers of reversibly necked material joined to one or more layers of elastic sheet at spaced locations. Reversibly necked materials are those that have been treated, such as with heat, while necked to impart memory to the material so that, when a force is applied to extend the material to its pre-necked dimensions, the treated, necked portions will generally recover to their necked dimensions upon termination of the force.

The term "stretch bonded" refers to an elastic member being bonded to another member while the elastic member is extended at least about 25 percent of its relaxed length. The term "stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered. Such a multilayer composite elastic material may be stretched to the extent that the nonelastic material gathered between the bond locations allows the elastic material to elongate. One type of stretch bonded laminate is disclosed, for example, by U.S. Pat. No. 4,720,415 to Vander Wielen et al., in which multiple layers of the same polymer produced from multiple banks of extruders are used. Other composite elastic materials are disclosed in U.S. Pat. No. 4,789,699 to Kieffer et al.; U.S. Pat. No. 4,781,966 to Taylor; U.S. Pat. Nos. 4,657,802 and 4,652,487 to Morman; and U.S. Pat. No. 4,655,760 to Morman et al. As used herein the term "composite elastic material" refers to an elastic material which may be a multi-component material or a multilayer material in which one layer is elastic.

The expansion panels 40 and 42 may include reinforcement segments 70 that are coterminous with the end edges 26 and 27 and extend the full width of the undergarment 20 (FIG. 2). In the illustrated embodiment, the reinforcement segments 70 comprise folded regions 71 where the expansion panel material is folded over and generally doubled in thickness. The folded regions 71 are maintained by suitable bonds 72, such as ultrasonic bonds, thermal bonds, adhesive bonds, mechanical bonds, or the like. Alternatively, the reinforcement segments 70 may be formed from a separate layer of material that is bonded to the expansion panels 40 and 42 to form regions that are generally doubled in thickness (not shown). Such separate material would desirably be formed of an extendible or an elastic material having properties similar but not necessarily identical to those of the expansion panels 40 and 42.

For attachment of the strap members 22 (FIG. 1), the expansion panels 40 and 42 of the illustrated embodiment define slits 74 (FIG. 2) formed near the corners of the undergarment 20. The integrity of the slits 74 may be enhanced by backing patches 76 that are bonded to the expansion panels 40 and 42 using adhesives, ultrasonic bonds, thermal bonds, mechanical bonds, or the like.

The reinforcement segments 70 may function to enhance the elastic properties of the expansion panels 40 and 42 along the end edges 26 and 27. In particular, the reinforcement segments 70 provide greater recovery forces at a given elongation, compared to the non-reinforced portions of the expansion panels 40 and 42. Provided the slits 74 or other forms of strap attachment fasteners are disposed in the reinforcement segments 70, this beneficially reduces gapping of the undergarment 20 in the waist regions 30 and 32.

The bond regions 46 and 47, which secure the expansion panels 40 and 42 to the storage assembly 44, may have a bracket shape, that is a [—shape and a ]—shape respectively when viewed in top plan view, such as in FIG. 2. At each end, the bracket shape is directed so as to be open in the direction of the absorbent structure 52. More precisely, the bond regions 46 and 47 have a longitudinal dimension that is greater in or adjacent the side margins 38 than in the transverse center of the undergarment 20. As a result, the inner edges of the expansion panels 40 and 42 form unadhered end flaps 80. Alternatively, the bond regions 46 and 47 may have a constant longitudinal dimension across the width of the undergarment 20 or be curved (not shown).

As best shown in FIG. 3, the end flaps 80 represent portions of the expansion panels 40 and 42 that are disposed longitudinally inward of the bond regions 46 and 47 and are at least partially unadhered to the storage assembly 44. As used herein, the term "unadhered" refers to an absence of bonds of sufficient strength to withstand the forces typically encountered during ordinary wearing of the undergarment. It is hypothesized that the end flaps 80 hinder movement of liquid toward the waist regions 30 and 32, and are particularly useful when the expansion panels 40 and 42 comprise liquid permeable materials. The end flaps 80 may also be formed or treated to be liquid impermeable. It is also hypothesized that the increased longitudinal dimension of the bond regions 46 and 47 in or adjacent the side margins 38 is useful to withstand the elongation forces of the expansion panels 40 and 42.

The strap members 22 illustrated in FIG. 1 are separate structures from the undergarment 20 and each comprise fastening components to releasably attach the strap members to the front and back waist regions 30 and 32. The fastening components include a retainer 84 in the form of a button bonded at each end of each strap member 22 (FIG. 1; only one half of each strap shown). The retainers 84 may be releasably secured in the slits 74 in the expansion panels 40 and 42. When the undergarment 20 is positioned on the wearer, the strap members 22 extend between the front and back slits 74 so that the retainers 84 may be releasably secured in the slits. Optionally, other types of retainers such as tapes, self-engaging geometric shaped materials, such as hooks, loops, bulbs, mushrooms, arrowheads, balls on stems, or the like, may be employed. The illustrated attachment system as well as alternatives thereto are described in U.S. Pat. No. 4,315,508 issued Feb. 16, 1982 to Bolick and U.S. Pat. No. 5,386,595 issued Feb. 7, 1995 to Kuen et al., the disclosures of which are incorporated herein by reference.

The strap members 22 (FIG. 1) are each generally rectangular strips of material, which material is desirably an elastic material capable of stretching more than 2 times its relaxed length, for example to approximately 2.8 to 5 times its relaxed length. The strap members 22 desirably have a length from about 5 to about 41 centimeters (cm.), and a width from about 1 to about 10 cm. For example, each strap member 22 may be 28 cm. long and 2.5 cm. wide. The cut ends of the strap members 80 may be bonded by ultrasonics, adhesives or other suitable means to prevent raveling.

Suitable materials for use in the strap members 22 include an interwoven polyester/rubber fabric with a nylon fluff backing available from Shelby Elastics, Inc. of Shelby, N.C., USA, under the trade designation K-78. Another suitable material is a 1.5 inch (3.81 cm) wide elastomeric strap comprising 50 gauge neoprene elastomer at 23 ends per band from JPS Elastomerics of Greensboro, N.C., USA; 4 strands of number 70 white nylon yarn; and number 4 and number 8 monofilaments; the strap generating a tension of about 550 grams at an elongation of 100 percent and a stress decay of 15.4 percent after 1 hour at an elongation of 100 percent. Another suitable strap material available from Shelby Elastics under the trade designation NP-50 comprises 50 gauge neoprene elastomers generating a tension of about 510 grams at an elongation of 100 percent and a stress decay of 14.7 percent after 1 hour at an elongation of 100 percent.

In use, the undergarment 20 is positioned on the wearer and secured with the attachment system. The strap members 22 are elongated as needed so that the buttons 84 may be releasably secured in the slits 74 of the undergarment 20. Due to the extension and/or elastic properties of both the strap members 22 and the expansion panels 40 and 42, each of these components is considered for purposes of the present invention as forming part of the multi-component suspension and attachment system that maintains the garment snugly on the wearer during use. The selection of materials for the suspension and attachment system is important for proper functioning of the absorbent article. It is desirable for the absorbent article not to sag during use, even when the storage assembly 44 contains a large amount of liquid. Further, it is desirable for the absorbent article to minimize gapping of the garment 20, which could otherwise create paths for liquid to escape from the garment.

Initially, it is desirable for the expansion panels 40 and 42 to elongate in the transverse direction 25 (FIG. 2) when the garment is applied. This provides greater psychological security because the expansion panels 40 and 42 cover larger portions of the buttocks and/or abdomen of the wearer. Further, in embodiments where the expansion panels comprise an elastic material, the garment is more comfortable due to the elastic forces extending about the full circumference of the wearer. Also, constructing the undergarment 20 such that the elasticity of the expansion panels 40 and 42 is substantially completely in the transverse direction decreases the likelihood that the garment will sag when the storage assembly 44 is loaded. Further, the increased size of the expansion panels 40 and 42 provides more surface area in contact with the wearer than a conventional undergarment, and consequently, because the amount of friction increases with contact area, the garment 20 should support more load before slipping than a conventional undergarment.

Additionally, as the expansion panels 40 and 42 elongate in the transverse direction 25, the undergarment 20 tends to become more underwear-like and/or pant-like. This allows the strap members 22 to become shorter than with non-expandable waist regions. The entire garment 20 will then provide the wearer with additional feelings of normalcy and psychological comfort. Further, the extensibility of the strap members 22 is now supplemented with the extensibility of the expansion panels 40 and 42 so that the absorbent article will fit a greater range of sizes of wearers. If the expansion panels 40 and 42 are formed of breathable materials, the waist regions 30 and 32 render the added benefit of allowing moisture to evaporate or migrate from the surface of the skin, thereby keeping the wearer cool and dry.

The expansion panels 40 and 42 desirably remain in an extended condition during use to continue to provide the increased body coverage. If, conversely, the expansion panels 40 and 42 were to retract too much during use and the strap members 22 were to elongate, the fit, comfort, and psychological security benefits associated with the increased body coverage would be lost. Moreover, the close-to-the-body fit would likely be impaired and gapping of the product would increase, which could lead to leakage of urine outside the product.

Figure 4:
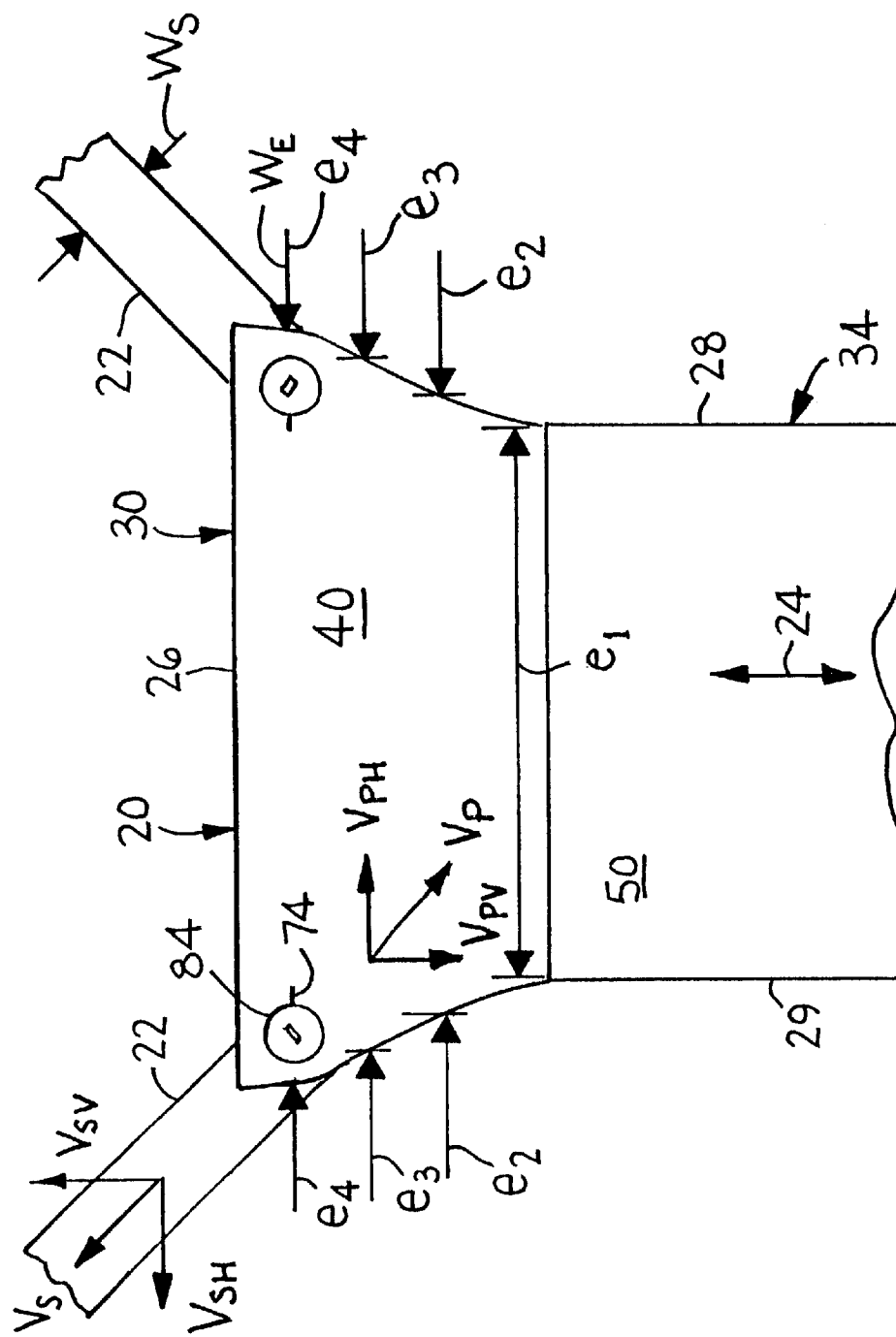
FIG. 4 representatively shows a portion of the absorbent article of FIG. 1 illustrating various dimensions and the forces acting on the suspension system during use.

Operation of the undergarment 20 and strap members 22 will now be described in greater detail in relation to FIG. 4, which representatively shows the forces acting on the suspension and attachment system during use. The strap members 22 are elongated during use and generally positioned at an angle relative to the longitudinal axis 24, such as from about 25 to 90 degrees. The elastic properties of each strap member 22 generate a force vector $V_S$ for each strap member which comprises a horizontal component $V_{SH}$ and a vertical component $V_{SV}$. Each corner of the first expansion panel 40 experiences a generally equal and opposite force vector $V_P$ which comprises a horizontal component $V_{PH}$ and a vertical component $V_{PV}$. The first expansion panel 40 will elongate in a direction substantially perpendicular to the longitudinal axis 24 of the undergarment 20 to the point where the horizontal force components $V_{SH}$ of the strap members and $V_{PH}$ of the first expansion panel are balanced. Significantly, the expansion panel 40 desirably has sufficient resistance to elongation in the longitudinal direction 24 that the expansion panel does not significantly elongate in the longitudinal direction in response to the vertical force component $V_{SV}$ of the strap member 22, thus minimizing sagging of the undergarment.

In order to obtain increased body coverage, it is desirable for the first and second expansion panels 40 and 42 to be adapted to have an extended width WE during use (FIG. 4) that is substantially greater than its unextended width $W_U$ (FIG. 2). Specifically, the extended width $W_E$ is desirably at least about 110 percent, more particularly at least about 125 percent, and even more particularly by at least about 135 percent, of the unextended width $W_U$. The extended width $W_E$ and the unextended width $W_U$ of the expansion panels 40 and 42 are both measured between the longitudinal side edges 28 and 29 of the garment 20 at the longitudinal location corresponding to the attachment points of the strap members 22 to the expansion panels 40 and 42. The unextended width $W_U$ is measured when the undergarment 20 is laid flat with no transverse force applied to the expansion panels (FIG. 2), whereas the extended width $W_E$ is measured during use or simulated use conditions. With further reference to FIG. 4, it will be apparent that the amount of transverse extension of the first and second expansion panels 40 and 42 is greatest near the end edges 26 and 27 of the undergarment 20. The amount of transverse extension of the first waist panel 40 is shown at four longitudinally spaced locations designated $e_1$, $e_2$, $e_3$ and $e_4$, beginning adjacent the crotch region 34 ($e_1$) and evenly spaced to the longitudinal location corresponding to the attachment points of the strap members 22 to the expansion panels 40 and 42 ($e_4$) By definition, the amount of transverse extension $e_4$ at the longitudinal location corresponding to the attachment points of the fasteners is the same as $W_E$. Provided the expansion panels 40 and 42 have generally uniform elongation properties, the amount of transverse extension at the longitudinally spaced locations will result in: $e_4 \geq e_3 \geq e_2 \geq e_1$.

The expansion panels 40 and 42 should have a length dimension L (FIG. 2) sufficient to provide the desired degree of body coverage. In particular, the expansion panels 40 and 42 suitably have a length dimension L of at least 5 centimeters (cm.), more particularly at least about 10 cm., such as from about 12.5 to about 20 cm, for improved performance. The proper length dimension L of the expansion panels 40 and 42 may also be characterized in relation to the width dimension $W_S$ of the strap members 22 (FIG. 4). It is desirable, for example, that the length dimension L of the expansion panels 40 and 42 be at least 200 percent of the width dimension $W_S$ of the strap members 22, more particularly at least 250 percent, and even more particularly at least about 300 percent, for improved performance.

The length dimension L (FIG. 2) is a measure of those portions of the waist regions 30 and 32 that transversely elongate without rupture when the garment is worn, measured parallel to the longitudinal axis 24. In the illustrated embodiment, the length dimension L of each expansion panel 40 and 42 extends from the respective bond region 46 and 47 to the respective end edge 26 and 27. The portions of the expansion panels 40 and 42 forming the end flaps 80 are not included in the length dimension L because they do not transversely elongate when the garment 20 is worn.

The strap members 22 are desirably adapted to retract over time to accommodate stress decay of the expansion panels 40 and 42. Thus, the expansion panels 40 and 42 desirably have greater stress decay values than the strap members 22. For purposes of the present invention, the term "stress decay" refers to the property of an elastic material to lose its recovery force over time. The strap members 22 should have better resistance to stress decay than the expansion panels 40 and 42 so that the strap members can retract to take up any slack as the expansion panels elongate while the product is worn. If, on the other hand, the strap members 22 would have greater stress decay values than the expansion panels 40 and 42, the panels would tend to retract to take up slack in the system and thereby diminish coverage of the buttocks and/or front waist region. A suitable procedure for determining the stress decay of an expansion panel or a strap member is the Material Stress Decay Test at 100% Elongation set forth hereinafter. Suitable strap members desirably have a stress decay value of less than about 20 percent after 1 hour at an elongation of 100 percent, meaning that they lose less than 20 percent of their original retractive force.

The suspension system must provide sufficient force against the body of the wearer to maintain the undergarment 20 in place during use. Consequently, it is important that at least one of the components of the suspension system, that is the strap members 20, the expansion panels 40 and 42, or both, develop and maintain sufficient retractive forces so that the garment 20 does not fall off in use. For example, if the expansion panel material would continuously elongate during use until the strap retracted to a point where its force was too low, the garment 20 would fall off. Contrariwise, if the strap force decays and/or it elongates continuously, the garment 20 will again become too loose. Therefore, the elastic properties of the strap and panel suspension and attachment system in series must maintain enough retractive force over time to keep the garment 20 in place on the wearer as it is loaded with urine.

Figure 5:
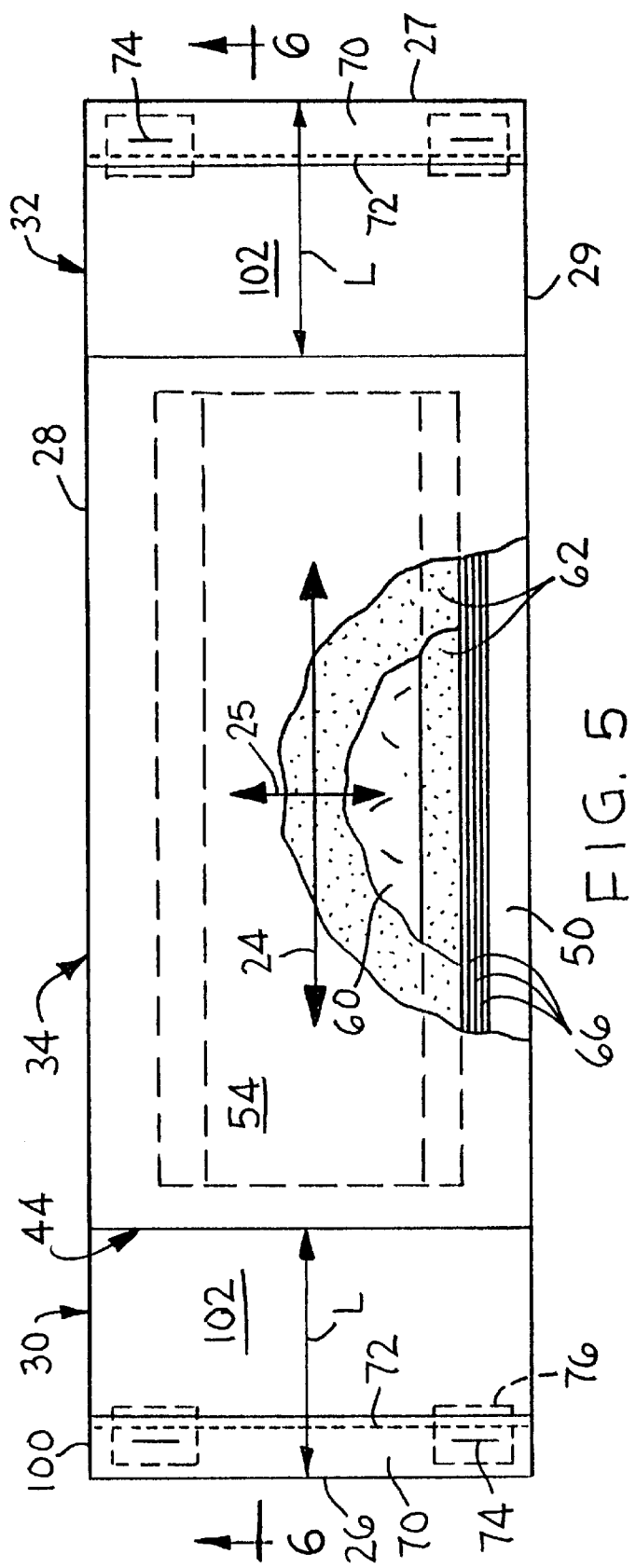
FIG. 5 representatively shows a plan view of a garment representing an alternative embodiment of the present invention, taken from the bodyside of the garment in a longitudinally stretched and laid flat condition and with portions broken away for purposes of illustration.
Figure 6:
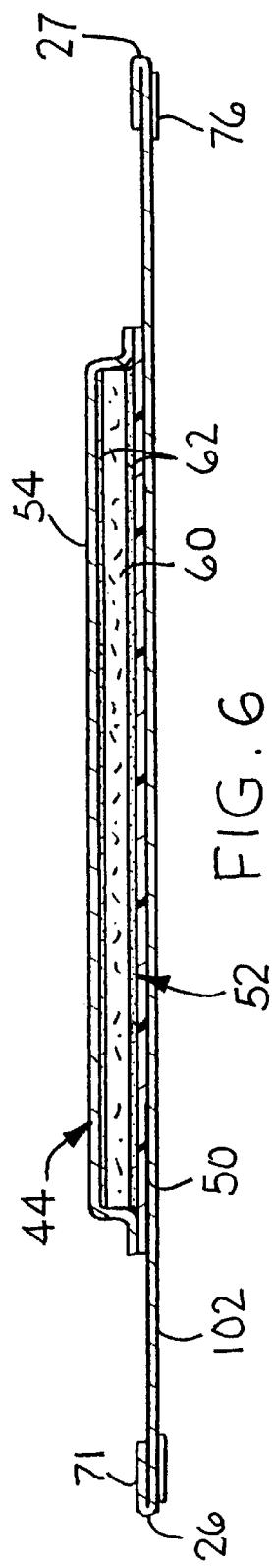
FIG. 6 representatively shows a section view taken generally from the plane of the line 6—6 in FIG. 5.

An alternative embodiment of the invention is illustrated in FIGS. 5 and 6 by an undergarment 100 that is adapted for use with separate strap members 22. Components similar to those previously described have been given the same reference numeral. The undergarment 100 has a longitudinal length dimension measured between the opposite end edges 26 and 27 parallel to the longitudinal axis 24. The undergarment 100 comprises a single expansion panel 102 that has a length substantially equal to the total longitudinal length dimension of the undergarment. The expansion panel 102 is a single unitary element and is thus disposed in the front and back waist regions 30 and 32 and the crotch region 34. In the illustrated embodiment, the expansion panel 102 forms the opposite end edges 26 and 27 and thus defines the longitudinal length dimension. The expansion panel 102 may also include folded regions 71 and have backing patches 76 attached thereto. The expansion panel 102 is adapted to elongate in a direction substantially perpendicular to the longitudinal axis 24.

A storage assembly 44 is disposed on the expansion panel 102 between the opposite end edges 26 and 27. The longitudinal length of the storage assembly 44 is less than the longitudinal length dimension of the undergarment 100. For purposes of the present invention, the front and back waist regions 30 and 32 are defined as those portions of the undergarment 100 that are disposed longitudinally beyond the ends of the storage assembly 44. Thus, the storage assembly 44 is disposed in the crotch region 34.

The storage assembly 44 in the illustrated embodiment comprises a moisture barrier 50, an absorbent structure 52, and a bodyside liner 54, and may be bonded to the expansion panel 102 using adhesives, ultrasonic bonds, thermal bonds, or other suitable means. Alternatively, the expansion panel 102 may comprise a liquid impermeable material and the storage assembly 44 may exclude a separate moisture barrier 50 (not shown). The illustrated absorbent structure 52 includes an absorbent batt 60 sandwiched between two tissue layers 62. The storage assembly 44 may also include leg elastic members 66 in the side margins.

In the front and back waist regions 30 and 32, the expansion panel 102 is unencumbered by the storage assembly 44 and is thus able to elongate substantially perpendicular to the longitudinal axis 24 to provide greater coverage over the abdomen and buttocks of the wearer. The waist regions 30 and 32, and specifically the portions of the expansion panel 102 that extend longitudinally beyond the storage assembly 44 and are adapted transversely elongate when the garment 100 is worn, desirably have a length dimension L (FIG. 5) of at least 5 cm., more particularly at least about 10 cm., such as from about 12.5 to about 20 cm., for improved performance. The length dimension L is desirably at least 200 percent of the width dimension $W_S$ of the strap members 22, more particularly at least 250 percent, and even more particularly at least about 300 percent, for improved performance. The crotch region 34 will generally not elongate in the transverse direction 25 because it is restrained by the storage assembly 44.

The expansion panel 102 may be formed from the same materials as described in relation to the expansion panels 40 and 42 of the embodiment of FIG. 1, and desirably comprises an elastomeric material. The full-length expansion panel 102 illustrated in FIGS. 5 and 6 could alternatively form one of the bodyside liner 54 or moisture barrier 50 layers (not shown). Still alternatively, the full-length expansion panel could comprise multiple layers, including layers forming the bodyside liner 54, the moisture barrier 50, or both.

Figure 7:
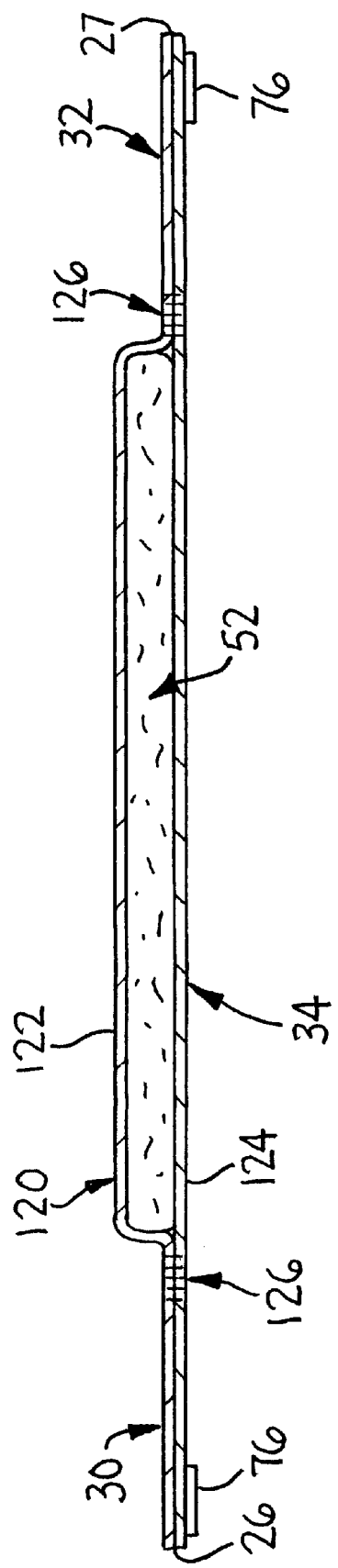
FIG. 7 representatively shows a section view similar to FIG. 6 but illustrating another alternative embodiment of the present invention.

For example, a further alternative embodiment of the invention is illustrated in section view in FIG. 7 by an undergarment 120 that is adapted for use with separate strap members 22 (not shown). The undergarment 120 comprises a pair of expansion panels 122 and 124 that extend between the opposite end edges 26 and 27 of the undergarment. Both expansion panels 122 and 124 are disposed in the front and back waist regions 30 and 32 and the crotch region 34. Also, both expansion panels 122 and 124 are adapted to elongate in a direction substantially perpendicular to the longitudinal axis of the undergarment 120. The strap members 22 may include buttons for attaching to button holes 74 (not shown) reinforced with backing patches 76.

An absorbent structure 52 is disposed between the expansion panels 122 and 124 in the crotch region 34. The crotch region 34 may also include leg elastic members 66 (not shown).

For both product performance and appearance reasons, it may be desirable to isolate the elasticity of the crotch region 34 from the extensibility and/or elasticity of the waist regions 30 and 32. In particular, it is believed to be desirable to isolate the waist regions 30 and 32 from the longitudinal elasticity provided by the leg elastic members 66, thereby minimizing the chance that the leg elastic members will contribute to pulling the garment down off the hip and waist regions of the wearer.

The crotch region 34 and waist regions 30 and 32 may be elastically isolated from one another by providing substantially nonextensible zones disposed between the crotch and waist regions. For example, nonextensible zones as indicated at reference numeral 126 may be provided by substantially diminishing or deadening the extension and/or elastic properties of the expansion panels 122 and 124 by means of ultrasonic bonds, adhesive bonds, thermal bonds, or the like. The nonextensible zones 126 are suitably positioned near the longitudinal ends of the absorbent structure 52 and extend across substantially the full width of the undergarment.

The expansion panels 122 and 124 in the embodiment of FIG. 7 function as the bodyside liner and moisture barrier sandwiching the absorbent structure 52 therebetween. Suitable materials for forming the expansion panels 122 and 124 are described in relation to the expansion panels 40 and 42 of the embodiment of FIG. 1, and desirably comprise extensible and/or elastomeric materials. The materials may be formed or treated to possess the desired degree of liquid permeability.

EXAMPLES

Having thus described the present invention and the process for making it, a series of examples were prepared to give a more detailed understanding of the invention. These examples and the test procedures for measuring them are set forth below. The particular amounts, proportions, compositions and parameters are meant to be exemplary, and are not intended to specifically limit the scope of the invention.

A System Stress Decay Test was conducted to compare several materials for use as expansion panels in the present invention. The System Stress Decay Test in some respects parallels operation of the multi-component suspension and attachment system during use conditions. The test, which is graphically illustrated in FIGS. 8 and 9, employs a Sintech material test system, also know as a tensile tester. An appropriate test system is the Model 1/S available from MTS Systems Corporation of Eden Prairie, Minnesota. The material test system is provided with an appropriately sized load cell, for example, a 4.54 kgm. (10 lb.) load cell available from MTS Systems Corporation. The material test system is operated using suitable control software, for example, TEST WORKS® version 3.03 for WINDOWS® available from MTS Systems Corporation.

Figure 8:
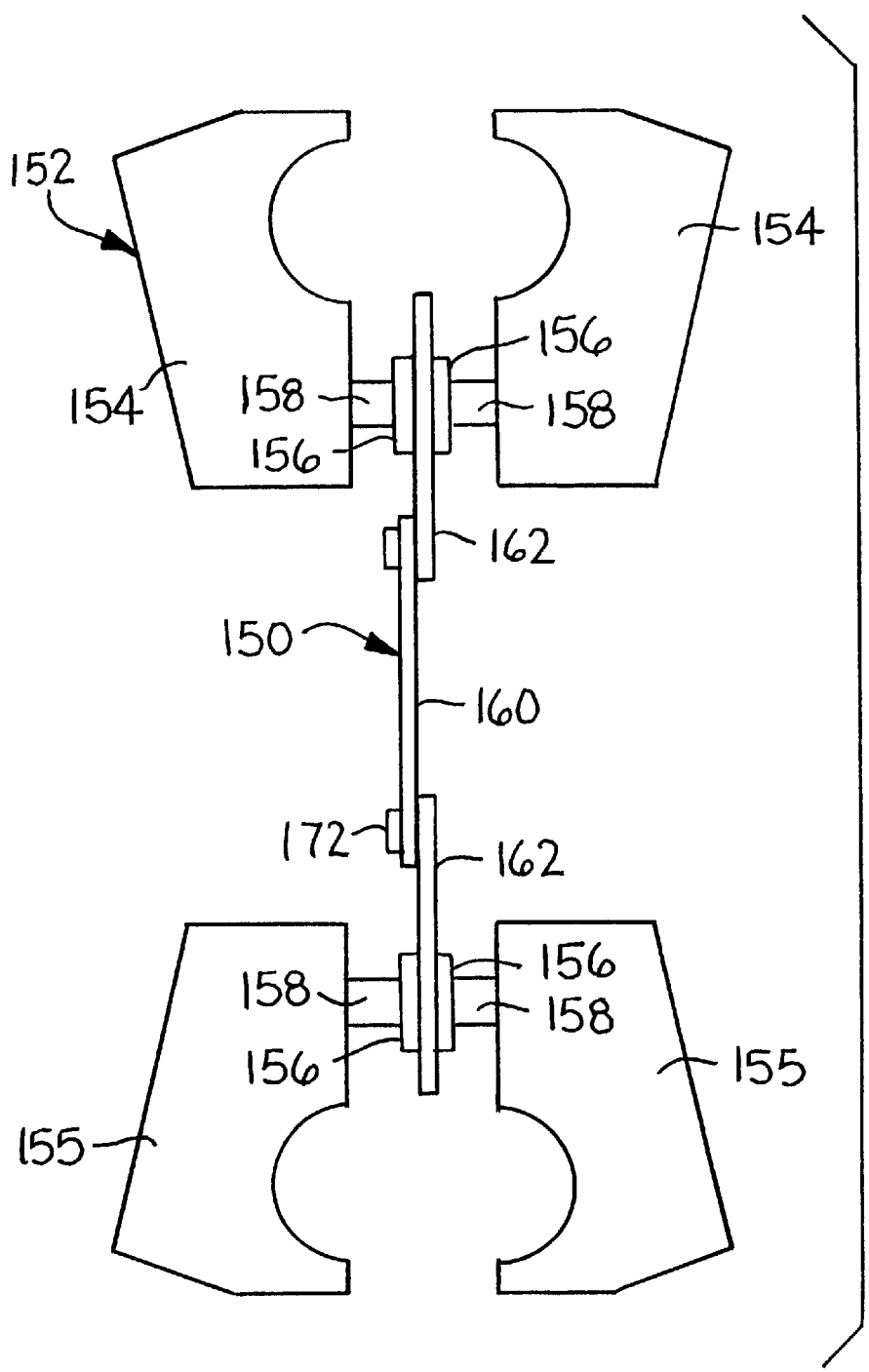
FIG. 8 representatively shows a side view of a tensile tester used for measuring stress decay of a test specimen.

With reference to FIG. 8, a test specimen 150 is illustrated in proper position for testing in the material test system 152. The material test system 152 includes upper and lower pneumatic grips 154 and 155 wherein the upper grips are vertically movable relative to the lower grips. Each set of pneumatic grips 154 and 155 includes an opposed pair of rubber-coated grip facings 156 that are adapted to move toward one another through the action of pneumatic cylinders 158.

Figure 9:
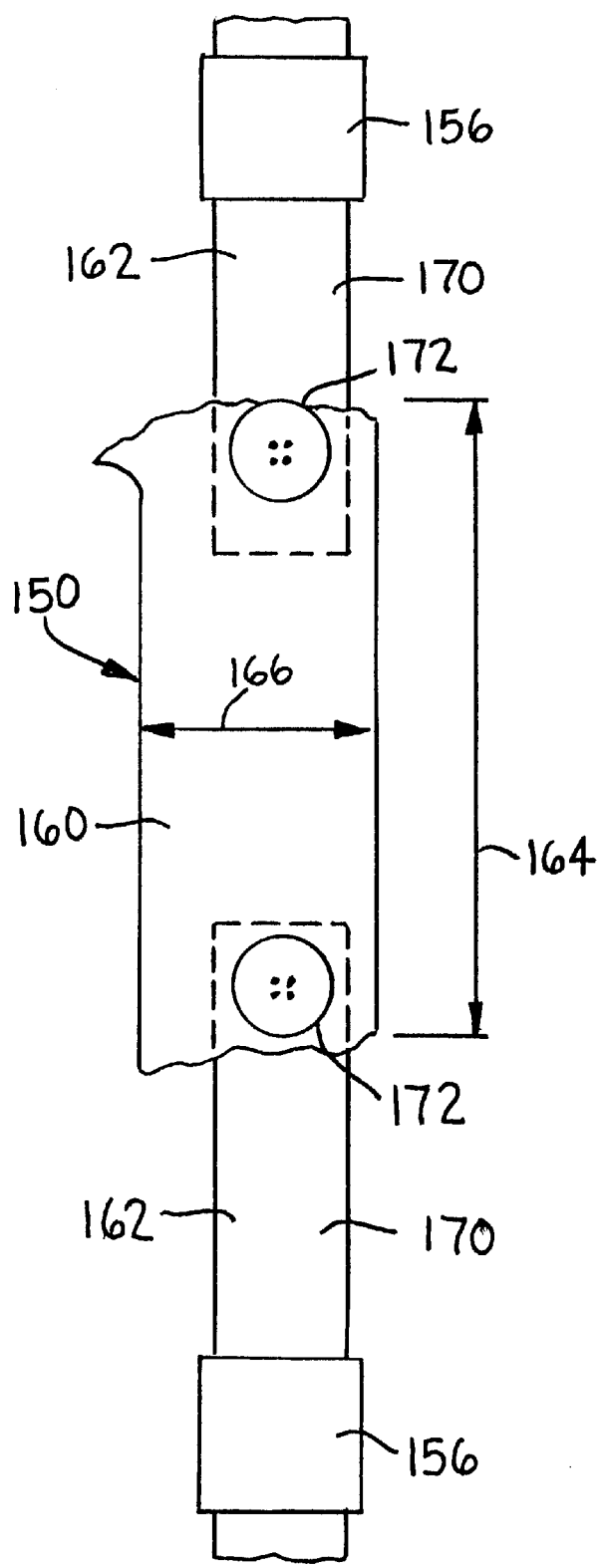
FIG. 9 representatively shows an enlarged, partial front view of the tensile tester and test specimen shown in FIG. 8.

With additional reference to FIG. 9, the test specimen 150 includes a test material 160 and a pair of partial strap members 162. The test material 160 is cut using a scissors so that it is rectangular with a long dimension 164 of 21.5 cm. and a shorter dimension 166 of 7.6 cm. Two button holes each measuring 2 cm. in length are cut in the test material 160 using a knife (not shown). The button holes are formed parallel to the long dimension 164 and spaced about 2 cm. from one long edge and about 2 cm., such as from 1.5 to 3 cm., from each short edge. The button holes are reinforced with a film tape (not shown) of the type commonly used on commercial undergarments that is adhesively bonded to the test material 160.

The partial strap members 162 each included a strip of elastic material 170 and a button 172. The elastic material 170 comprised 50 gauge neoprene elastomer at 23 ends per band from JPS Elastomerics, 4 strands of number 70 white nylon yarn, and number 4 and number 8 monofilaments. Each strip of elastic material 170 had a length of greater than 12.7 cm. and a width of 3.81 cm (1.5 in). The strap ends were ultrasonically bonded to prevent raveling. The buttons 172 were sewn onto the end regions of the strips of elastic material 170 so that the button centers were transversely centered and spaced from one end by 1.5 cm. The buttons 172 measured 22.2 mm. in diameter and were purchased from Engineering Industries of Verona, Wis. under the trade designation green membrane buttons.

The System Stress Decay Test is begun by calibrating and preparing the equipment as specified by the manufacturer. The test specimen 150 is assembled by securing the buttons 172 in the button holes of the test material 160. The test specimen is then positioned in the upper and lower pneumatic grips 154 and 156 in the manner indicated in FIGS. 8 and 9. Specifically, the partial strap members 162 are secured between the grip facings 156 so that the length of the elastic strap material 170 from each grip facing to the center of the closest button is 12.7 cm. The distance between the jaws of the tensile tester should be set to 41.9 cm. during set up in order not to prematurely elongate the test specimen 150.

During the test, the lower pneumatic grips 155 are maintained stationary while the upper pneumatic grips 154, referred to as the crosshead, is moved vertically relative thereto. The crosshead is first moved to a beginning position, which represents a separation distance that causes the materials to lose any large wrinkles or "slack" and causes the buttons to move toward the outer limits of the button holes, without creating too much preload. The load measured by the load cell should be from about 5 to about 20 grams at the beginning position.

Four length dimensions are then noted and recorded for the beginning position: a total length, which is the distance between the grip facings 156; a panel length, which is the distance between the centers of the buttons; and strap #1 and strap #2 lengths, which represent the length of each strap from the grip facing to the center of the button. The total length is determined by the tensile tester equipment; the panel length is measured by the operator using a ruler; and the strap #1 and strap #2 lengths are both calculated using the formula: [(total length−panel length)/2].

At this time, the control software is initiated. In general, the crosshead is raised at a constant rate of 500 millimeters per minute (mm/min) to 50 percent position. For instance, for a total length at the beginning position of 41.9 cm., the test specimen 150 is elongated 21 cm. at a constant rate over approximately 25 seconds. The load measured by the load cell is noted and recorded at: 0 seconds, which represents pre-elongation; 15 seconds; 30 seconds; 1 minute; 5 minutes; 10 minutes; 20 minutes; 30 minutes; 40 minutes; 50 minutes; and 1 hour. The total length, the panel length and the strap #1 and strap #2 lengths are noted and recorded immediately upon reaching 50 percent elongation; 30 minutes after initiating the control software; and 1 hour after initiating the control software. Note that the total length does not change after the crosshead reaches 50 percent elongation. A stress decay value for the test material, expressed as a percentage, is calculated using the formula: [(load at 1 minute−load at 1 hour)/load at 1 minute]×100.

Example 1

A test material designated Example 1 comprised a neck bonded laminate material consisting of an elastomeric 30 gsm polyurethane film sandwiched between a pair of 28.7 gsm spunbond webs formed of polypropylene fibers. The spunbond webs were neck stretched to 40 percent of their original width and then ultrasonically bonded through the film to each other. The material had a measured elongation at peak load of about 186 percent.

Example 2

A test material designated Example 2 comprised a neck stretched laminate material consisting of a 16.9 gsm spunbond web formed of polypropylene fibers and a 16.9 gsm meltblown web formed of polypropylene fibers. The spunbond web was neck stretched 50 percent of its original width and then bonded to the meltblown web by passing through a compression nip. The material had a measured elongation at peak load of about 121 percent.

Example 3

A test material designated Example 3 comprised a reversibly neck stretched spunbound laminate material consisting of a 20.3 gsm spunbond web formed of polypropylene fibers and a 15.2 gsm meltblown web formed of polypropylene fibers. The spunbond web was neck stretched 54 percent of its original width, heated, cooled, and then bonded to the meltblown web by passing through a compression nip. The material had a measured elongation at a peak load of about 110 percent.

Example 4

A test material designated Example 4 comprised a stretch bonded laminate material consisting of 40 gsm elastomeric meltblown filaments, made of elastomeric block copolymers available from Shell Chemical Company and identified under the tradename KRATON G-2755, that were sandwiched between a pair of 13.5 gsm polypropylene spunbond webs and bonded together by passing through a compression nip while the elastomer was being stretched. Such elastomeric structures are disclosed in U.S. Pat. No. 5,332,613 to Taylor et al. The material had a measured elongation at a peak load of about 235 percent.

Example 5

A test material designated Example 5 comprised three layers of the material of Example 4 that were sandwiched together and placed in the jaws of the tensile tester. The material had a peak load that exceeded an 11.34 kgm. (25 lb.) load cell.

Example 6 (Comparative Example)

A relatively non-elastic, non-elongatable comparison material designated Example 6 comprised an adhesive laminate of a 16.9 gsm polypropylene spunbond web; a 0.023 mm. thick polyethylene film that was corona treated on both sides; and a 28.7 gsm spunbond web formed of uncrimped side-by-side polypropylene/polyethylene bicomponent fibers.

The results of the System Stress Decay Test for the materials of Examples 1–6 are summarized below in Tables 1–7. The change in length of the Example 6 comparison material reported in Table 6 is believed to be due to widening and/or tearing of the button holes and stressing the material. The relatively shorter panel length of the Example 5 material at the beginning position was observed to be due to curling of the material.

TABLE 1

System Stress Decay Test: Lengths (millimeters)
Example 1 Test Material

| Time | Strap #1 | Panel | Strap #2 | Total |
|---|---|---|---|---|
| Beginning | 126 | 167 | 126 | 419 |
| After Stretch | 205 | 219 | 205 | 629 |
| After 30 Min. | 203.5 | 222 | 203.5 | 629 |
| After 1 Hour | 203 | 223 | 203 | 629 |

TABLE 2

System Stress Decay Test: Lengths (millimeters)
Example 2 Test Material

| Time | Strap #1 | Panel | Strap #2 | Total |
|---|---|---|---|---|
| Beginning | 126 | 167 | 126 | 419 |
| After Stretch | 204 | 221 | 204 | 629 |
| After 30 Min. | 200 | 231 | 200 | 629 |
| After 1 Hour | 199 | 231 | 199 | 629 |

TABLE 3

System Stress Decay Test: Lengths (millimeters)
Example 3 Test Material

| Time | Strap #1 | Panel | Strap #2 | Total |
|---|---|---|---|---|
| Beginning | 126 | 167 | 126 | 419 |
| After Stretch | 193.5 | 242 | 193.5 | 629 |
| After 30 Min. | 188 | 253 | 188 | 629 |
| After 1 Hour | 186 | 257 | 186 | 629 |

TABLE 4

System Stress Decay Test: Lengths (millimeters)
Example 4 Test Material

| Time | Strap #1 | Panel | Strap #2 | Total |
|---|---|---|---|---|
| Beginning | 126 | 167 | 126 | 419 |
| After Stretch | 168.5 | 292 | 168.5 | 629 |
| After 30 Min. | 167 | 295 | 167 | 629 |
| After 1 Hour | 166.5 | 296 | 166.5 | 629 |

TABLE 5

System Stress Decay Test: Lengths (millimeters)
Example 5 Test Material

| Time | Strap #1 | Panel | Strap #2 | Total |
|---|---|---|---|---|
| Beginning | 132 | 155 | 132 | 419 |
| After Stretch | 217 | 195 | 217 | 629 |
| After 30 Min. | 216 | 197 | 216 | 629 |
| After 1 Hour | 216 | 197 | 216 | 629 |

TABLE 6

System Stress Decay Test: Lengths (millimeters)
Example 6 Test Material

| Time | Strap #1 | Panel | Strap #2 | Total |
|---|---|---|---|---|
| Beginning | 126.5 | 166 | 126.5 | 419 |
| After Stretch | 226 | 177 | 226 | 629 |
| After 30 Min. | 225 | 179 | 225 | 629 |
| After 1 Hour | 224.5 | 180 | 224.5 | 629 |

TABLE 7

System Stress Decay Test: Load Values (grams)
Examples 1–6

| Time | Ex. 1 | Ex. 2 | Ex. 3 | Ex. 4 | Ex. 5 | Ex. 6 |
|---|---|---|---|---|---|---|
| 0 sec. | 10.03 | 9.70 | 6.69 | 12.71 | 17.06 | 13.04 |
| 15 sec. | 391.05 | 372.59 | 330.12 | 300.92 | 407.12 | 448.24 |
| 30 sec. | 502.49 | 502.44 | 460.79 | 365.03 | 521.87 | 585.91 |
| 1 min. | 468.60 | 467.94 | 424.98 | 339.95 | 492.66 | 549.77 |
| 5 min. | 430.14 | 428.40 | 383.92 | 314.19 | 456.70 | 505.60 |
| 10 min. | 416.82 | 412.35 | 367.59 | 304.79 | 442.40 | 489.03 |
| 20 min. | 403.32 | 393.62 | 350.48 | 295.27 | 429.49 | 472.98 |
| 30 min. | 397.97 | 384.62 | 342.45 | 289.61 | 421.16 | 464.81 |
| 40 min. | 390.54 | 380.62 | 334.42 | 285.60 | 415.69 | 458.28 |
| 50 min. | 385.93 | 373.55 | 328.97 | 281.63 | 412.02 | 452.74 |
| 1 hour | 382.95 | 369.55 | 322.18 | 280.25 | 410.02 | 453.38 |
| Decay Value (%) | 18 | 21 | 24 | 18 | 17 | 18 |

From the data presented above, it is evident that although all of the materials tested showed some degree of stress decay, they all maintain a retractive load and hence will hold up an undergarment. Materials with lower decay values, such as Example 1, lose less of their retractive force over time and will hold the garment up better over longer periods than other materials, such as Example 3, which loses more retractive force over time. Materials with greater load values, such as Example 1, will also hold the garment up better than other materials, such as Example 4, which has a lower load value (retractive force) to begin with.

A Material Stress Decay Test At 50 Percent Elongation was conducted to compare individual materials for use as expansion panels in the present invention. The test equipment is the same as that employed in the System Stress Decay Test described above. Each test specimen represents a material cut to have a width of 7.62 cm. and a length of at least 18.7 cm. The test is begun by calibrating and preparing the equipment as specified by the manufacturer. The test specimen is positioned in the upper and lower pneumatic grips 154 and 156 so that about 3 cm. of test specimen material is held between each of the grip facings 156. This results in a material distance between the grip facings 156 of 12.7 cm.

During the test, the lower pneumatic grips 155 are maintained stationary while the crosshead 154 is moved vertically relative thereto. The crosshead is first moved to a beginning position, which represents a separation distance that causes the test specimen material to lose any large wrinkles or "slack" without creating too much preload. The load measured by the load cell should be from about 5 to about 20 grams at the beginning position.

The control software is initiated. In general, the crosshead is raised at a constant rate of 500 mm/min. to 50 percent elongation, that is, one and one-half (1.5) times the total length of the material measured between the grip facings at the beginning position. For instance, for a total length at the beginning position of 12.7 cm., the test specimen material is elongated 6.35 cm. at a constant rate over approximately 7.6 seconds. The load measured by the load cell is noted and recorded at: 0 seconds, which represents pre-elongation; 15 seconds; 30 seconds; 1 minute, 5 minutes; 10 minutes; 20 minutes; 30 minutes; 40 minutes; 50 minutes; and 1 hour. A material stress decay value at 50 percent elongation for the test material, expressed as a percentage, is calculated using the formula: [(load at 1 minute−load at 1 hour)/load at 1 minute]×100.

Example 7

A test material designated Example 7 comprised a 3.81 cm. by 12.7 cm. strip of elastic material comprising nylon, polyester and elastic materials that was purchased from Shelby Elastics under the trade designation NP 50. The material had a peak load that exceeded an 11.34 kgm. (25 lb.) load cell.

Example 8

A test material designated Example 8 comprised a 3.81 cm. by 12.7 cm. elastomeric strap material comprising 50 gauge neoprene elastimer at 23 ends per band from JPS Elastomerics; 4 strands of number 70 white nylon yarn; and number 4 and number 8 monofilaments. The test strap material had a peak load that exceeded an 11.34 kgm. (25 lb.) load cell.

The results of the Material Stress Decay Test At 50 Percent Elongation for the materials of Examples 1–8 are summarized below in Table 8. Due to the low elongation of the Example 6 material, it was not extended to the full 50 percent elongation but rather to a lesser value.

TABLE 8

Material Stress Decay Test at 50% Elongation:
Load Values (grams)
Examples 1–8

| Time | Ex. 1 | Ex. 2 | Ex. 3 | Ex. 4 | Ex. 5 | Ex. 6 | Ex. 7 | Ex. 8 |
|---|---|---|---|---|---|---|---|---|
| 0 sec. | 12.0 | 9.5 | 9.4 | 12.0 | 20.4 | 7.5 | 14.4 | 13.6 |
| 15 sec. | 672.3 | 691.0 | 328.3 | 294.9 | 884.5 | 4746.4 | 443.3 | 479.1 |
| 30 sec. | 637.0 | 620.7 | 297.8 | 282.8 | 850.3 | 4505.2 | 431.8 | 464.7 |
| 1 min. | 611.0 | 572.0 | 274.4 | 273.7 | 823.7 | 4343.0 | 422.3 | 455.6 |
| 5 min. | 563.9 | 479.8 | 228.9 | 257.2 | 778.1 | 3962.5 | 403.4 | 431.9 |
| 10 min. | 545.0 | 445.3 | 212.3 | 251.3 | 760.3 | 3714.0 | 393.7 | 422.9 |
| 20 min. | 527.0 | 414.0 | 197.4 | 243.5 | 741.2 | 3477.5 | 385.6 | 411.6 |
| 30 min. | 516.7 | 396.2 | 188.0 | 240.2 | 735.7 | 3346.6 | 379.7 | 406.0 |
| 40 min. | 510.8 | 383.7 | 180.7 | 235.6 | 720.6 | 3256.7 | 375.6 | 402.3 |
| 50 min. | 506.3 | 374.6 | 177.2 | 234.6 | 715.5 | 3193.2 | 371.6 | 398.6 |
| 1 hour | 500.6 | 367.1 | 172.9 | 231.1 | 710.8 | 3137.6 | 369.7 | 396.6 |
| Decay Value (%) | 18.1 | 35.8 | 37.0 | 15.6 | 13.7 | 27.8 | 12.5 | 12.9 |

A Material Stress Decay Test At 100 Percent Elongation was also conducted to compare several materials for use as strap members in the present invention. This test is the same as the Material Stress Decay Test at 50 percent elongation except that the crosshead is raised at a constant rate of 50 mm/min. to 100 percent elongation, that is, two times the total length of the test material between the grip facings at the beginning position. Accordingly, for a total length at the beginning position of 12.7 cm., the test specimen material is elongated 12.7 cm. at a constant rate over approximately 15.2 seconds. A material stress decay value at 100 percent elongation for the test material, expressed as a percentage, is calculated using the formula: [(load at 1 minute–load at 1 hour)/load at 1 minute]×100.

The results of the Material Stress Decay Test At 100 Percent Elongation for the materials of Examples 7 and 8 are summarized below in Table 9.

TABLE 9

Material Stress Decay at 100% Elongation:
Load Values (grams)
Examples 7 and 8

| Time | Example 7 | Example 8 |
|---|---|---|
| 0 seconds | 16.4 | 20.3 |
| 15 seconds | 663.5 | 719.3 |
| 30 seconds | 617.9 | 673.7 |
| 1 minute | 596.8 | 650.7 |
| 5 minute | 562.5 | 610.1 |
| 10 minute | 547.5 | 593.3 |
| 20 minute | 531.7 | 577.2 |
| 30 minute | 523.5 | 566.9 |
| 40 minute | 516.7 | 560.8 |
| 50 minute | 513.5 | 556.1 |
| 1 hour | 509.2 | 550.7 |
| Decay Value (%) | 14.7 | 15.4 |

The data in Tables 8 and 9 illustrate some of the material properties that are believed to be important with regard to the present invention. Examples 1–6 (Table 8) are materials which could be used as breathable, stretchable expansion panel materials. These materials were stretched to 150 percent of their original length and then allowed to decay. Examples 7 and 8 in Table 8 are typical of the materials used to make the detachable elastic straps. Note that they have stress decay values lower than the panel materials, indicating that they would tend to be more resistant to elastic decay over time. The expansion panel material, for example one of Examples 1–6, function in series with the strap material, for example one of Examples 7 and 8, and will reach an equilibrium value. As the expansion panel material stress decays, the straps, which tend to decay less, will retract and maintain the suspension and attachment system under tension. This of course keeps the undergarment from falling down, provided the peak load resulting from the strap and expansion panel system is greater than the downward force on the worn undergarment and provided the length of the strap and expansion panel system is not so long that it easily extends to the point where it falls off the wearer.

Comparative Example 6 (Table 8) shows what happens when the expansion panel material is pulled past its elongation limit. Destruction of the expansion panel material begins as the forces rise to a very high level, well beyond what the strap could maintain. In the case of Comparative Example 6, the material could not be extended to 150 percent of its initial length but only to some lesser value. The straps of Example 7 and 8 elongated to 50 percent elongation, however, could extend expansion panel materials of Examples 2, 3 and 4 more than 50 percent, because at one hour the straps have a greater retractive force. Because panel materials of Examples 1 and 5 have forces greater than the straps, they would not be stretched to 50 percent elongation by straps elongated only 50 percent. Referring to Table 9, however, note that the straps elongated 100 percent do have enough force to stretch out the expansion panel material of Example 1 to 50 percent. Because the expansion panel material of Example 5 at 50 percent elongation still has a retractive force greater than the straps at 100 percent (Table 9), for a force equilibrium to be generated the straps would have to elongate more than 100 percent and the expansion panel material of Example 5 (Table 8) less than 50 percent.

In summary, depending on the retractive forces generated and the body size of the wearer, the strap and the expansion panel materials will elongate until they reach an equilibrium force where the extended strap and expansion panel materials generate equal forces. As the materials stress decay, this relationship will change. Materials with higher decay values will lose force and elongate while those with lower decay values will tend to retract and hence maintain tension in the system.

Test Procedures

Water Vapor Transmission Rate Test

The water vapor transmission rate (WVTR) of a fabric gives an indication of how comfortable a fabric would be to wear. A suitable technique for determining the WVTR of a material is ASTM Standard E96-80. For the purposes of the present invention, circular samples measuring 3 inches in diameter are cut from the test fabric and a control material which is a piece of CELGUARD® 2500 film from Hoechst Celanese Corporation of Sommerville, N.J., USA. CELGUARD® 2500 is a 0.0025 cm thick microporous polypropylene film.

Five samples are prepared for the test and the control materials. The test dish is a No. 60-1 Vapometer pan distributed by Thwing-Albert Instrument Company, Philadelphia, Pennsylvania, U.S.A. One hundred milliliters of water are poured into each Vapometer pan, and each of the samples of the test material and control material are placed across the open tops of the individual pans. Do not apply stopcock grease unless sample contamination can be avoided. Screw-on flanges are tightened to form a seal along the edges of the pans, leaving the associated test material or control material exposed to the ambient atmosphere over a 6.5 cm diameter circle having an exposed area of about 33.17 square centimeters. The pans are placed in a forced air oven set at 32° C. (100° F.) for 1 hour to equilibrate. The oven is a constant temperature oven with external air circulating through it to prevent water vapor accumulation inside. A suitable forced air oven is, for example, a Blue M Power-O-Matic 60 oven distributed by Blue M Electric Co. of Blue Island, Illinois, U.S.A. Upon completion of the equilibration, the pans are removed from the oven, weighed and immediately returned to the oven. After 24 hours, the pans are removed from the oven and weighed again. The preliminary test WVTR value is calculated as follows:

$$\text{Test } WVTR = (\text{grams weight loss over 24 hours}) \times 315.5 \ (g/m^2/24 \text{ hours})$$

The relative humidity within the oven is not specifically controlled.

Under predetermined set conditions of 32° C. (100° F.) and ambient relative humidity, the WVTR for CEL-GUARD® 2500 has been defined to be 5000 gm/m²/24 hours. Accordingly, the CELGUARD® 2500 is run as a control sample with each test, and the preliminary test values are corrected to the set conditions using the following equation:

$$WVTR = (\text{Test } WVTR/\text{control CELGUARD® } WVTR) \times 5000 \ gm/m^2/24 \ hr.$$

Liquid Wicking Test

Figure 10:
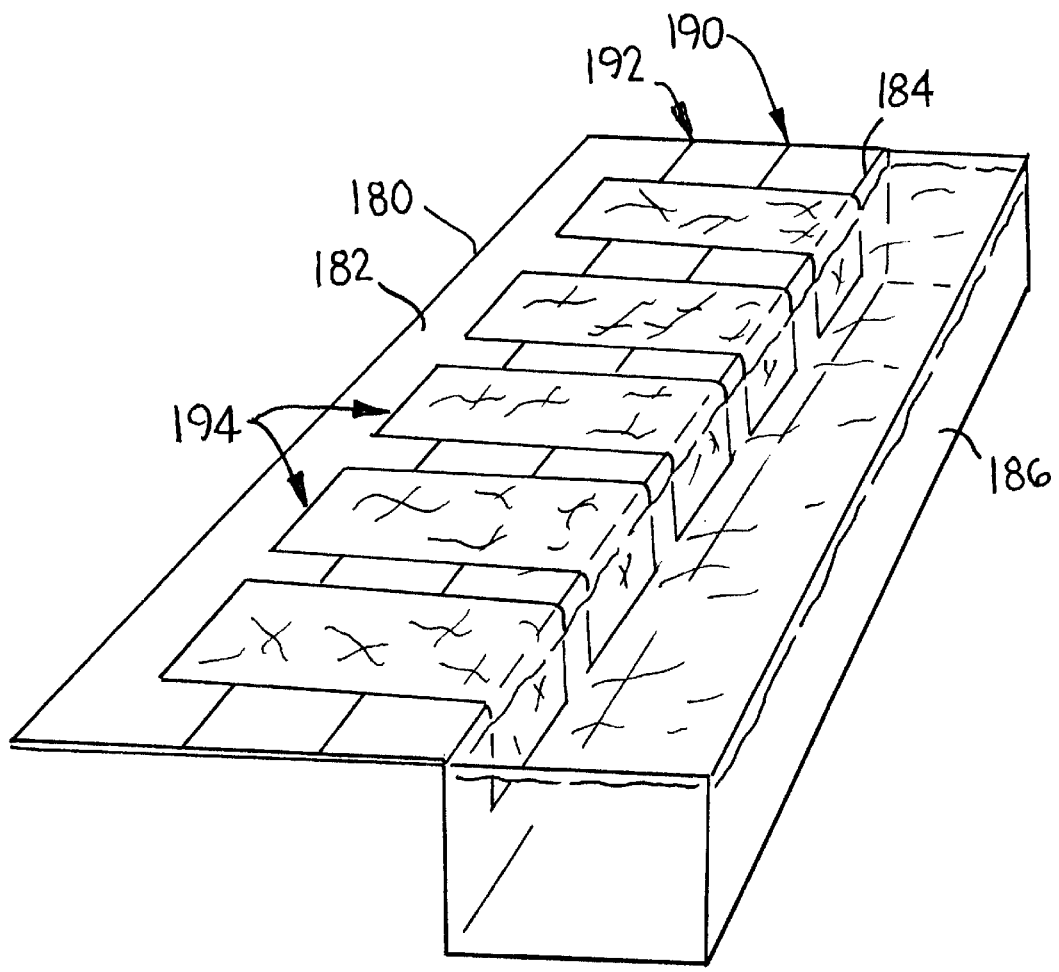
FIG. 10 representatively shows a test structure for measuring a liquid wicking rate of a material.

The Wicking Test measures the lateral movement of room temperature-distilled water through a material which is supported by a vinyl coated stainless steel plate. The plate 180, which is shown in FIG. 10, has a top surface 182 with an edge 184. A container 186 of distilled water is positioned beneath the edge 184 of the plate 180 such that the distance between the top surface and the water level is 1 cm. The plate 180 has lines 190 and 192 marking 5 and 10 cm., respectively, from the edge 184 of the plate.

In the test, five 50.8 by 152.4 mm. specimens 194 of the material to be tested are mounted on the top surface of the level plate. A narrow end of each specimen is weighted and positioned over the edge of the plate and into the liquid. When the sample ends are dropped into the liquid, a timer is started.

The progress of the liquid front is observed and the time, measured to the nearest 0.1 minute, is recorded as the liquid front begins to cross 5 and 10 cm. marks. If the liquid front has not reached the 10 cm. mark in 30 minutes, the test is stopped and maximum distance is recorded. The wicking value for a material is the average distance traveled after 30 minutes by the 5 specimens tested.

The foregoing detailed description has been for the purpose of illustration. Thus, a number of modifications and changes may be made without departing from the spirit of the scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. An absorbent article, comprising:

a garment having an absorbent structure, a longitudinal axis, a first waist region comprising an expansion panel having a length dimension of at least about 5 centimeters, a second waist region, and a crotch region intermediate and interconnecting the first and second of waist regions, the expansion panel forming an end flap that is disposed over and at least partially unadhered to the crotch region, the expansion panel adapted to elongate in a direction substantially perpendicular to the longitudinal axis; and a pair of separate elastomeric strap members each having opposite ends refastenably attached to the waist regions.

2. An absorbent article, comprising:

a garment having an absorbent structure, a longitudinal axis, a first waist region, a second waist region, and a crotch region intermediate and interconnecting the first and second waist regions, the first and second waist regions each comprising an expansion panel having a length dimension of at least about 5 centimeters adapted to elongate in a direction substantially perpendicular to the longitudinal axis, the expansion panel forming an end flap that is disposed over and at least partially unadhered to the crotch region; and a pair of separate elastomeric strap members each having opposite ends refastenably attached to the waist regions.

3. The absorbent article of claim 1 or 2, wherein the first waist region comprises an elastomeric material.

4. The absorbent article of claim 3, wherein the second waist region comprises an elastomeric material.

5. The absorbent article of claim 4, wherein the elastomeric materials of the first and second waist regions have different elastomeric properties.

6. The absorbent article of claim 1 or 2, wherein each strap member has a width dimension, and the expansion panel has a length dimension that is a least 200 percent of the width dimension of the strap member.

7. The absorbent article of claim 6, wherein the length dimension of the expansion panel is at least 250 percent of the width dimension of the strap member.

8. The absorbent article of claim 1 or 2, wherein the expansion panel has an unextended width and is adapted to have an extended width that is greater than the unextended width when subjected to a force perpendicular to the longitudinal axis.

9. The absorbent article of claim 8, wherein the extended width is at least about 110 percent of the unextended width.

10. The absorbent article of claim 8, wherein the extended width is at least about 125 percent of the unextended width.

11. The absorbent article of claim 1 or 2, wherein the first waist region is adapted to elongate in a direction forming an angle with the longitudinal axis of between about 70 and 90 degrees.

12. The absorbent article of claim 11, wherein the first waist region is adapted to elongate in a direction forming an angle with the longitudinal axis of between about 80 and 90 degrees.

13. The absorbent article of claim 1 or 2, wherein the crotch region comprises a bodyside liner, a moisture barrier and the absorbent structure disposed between the bodyside liner and the moisture barrier, the absorbent structure and the moisture barrier terminating longitudinally inward of the first and second waist regions.

14. The absorbent article of claim 1 or 2, wherein the expansion panel has a length dimension of at least about 10 centimeters.

15. The absorbent article of claim 1 or 2, wherein the expansion panel has a length dimension of from about 12.5 to about 20 centimeters.

16. The absorbent article of claim 1 or 2, wherein the strap members have a stress decay value, and the expansion panel has a stress decay value that is greater than that of the strap members.

17. The absorbent article of claim 1 or 2, wherein the expansion panel is adapted to extend and remain in an extended condition during use.

18. The absorbent article of claim 1 or 2, wherein the crotch region is adapted to be substantially nonextensible perpendicular to the longitudinal axis.

19. The absorbent article of claim 1 or 2, wherein the expansion panel comprises a reinforcement segment wherein the expansion panel is generally doubled in thickness.

20. The absorbent article of claim 19, wherein the garment includes fasteners disposed in the reinforcement segment and adapted to releasably engage the strap members.

21. The absorbent article of claim 1 or 2, wherein the expansion panel comprises a breathable material.

22. The absorbent article of claim 1 or 2, wherein the expansion panel has a wicking rate of less than about 3 centimeters per 30 minutes.

23. The absorbent article of claim 1 or 2, wherein the garment is adapted to have a generally uniform width dimension through the crotch and waist regions when laid flat and longitudinally stretched.

24. The absorbent article of claim 1 or 2, wherein the first waist region is adapted to assume a roughly trapezoidal shape when subjected to a force perpendicular to the longitudinal axis.

25. The absorbent article of claim 2, wherein the garment is adapted to have a rectangular shape when laid flat and longitudinally stretched and an hourglass or dog bone shape when laid flat and longitudinally and transversely stretched.

26. An absorbent article, comprising:
   a garment having a longitudinal axis, a first waist region, a second waist region, and a crotch region intermediate and interconnecting the first and second waist regions, the garment comprising:
      an expansion panel disposed in both the first and second waist regions and adapted to elongate in a direction substantially perpendicular to the longitudinal axis; and
      an absorbent structure disposed on the expansion panel in the crotch region and a substantially nonextensible zone disposed between the crotch region and each of the waist regions; and
      a pair of separate elastomeric strap members each having opposite ends refastenably attached to the waist regions.

27. The absorbent article of claim 26, wherein the expansion panel has a length substantially equal to a longitudinal length dimension of the garment.

28. The absorbent article of claim 26, wherein the expansion panel comprises a liquid impermeable material.

29. The absorbent article of claim 26, wherein the absorbent structure comprises a liquid impermeable moisture barrier bonded to the expansion panel.

30. The absorbent article of claim 26, further comprising a second expansion panel adapted to elongate in a direction substantially perpendicular to the longitudinal axis, the absorbent structure sandwiched between the expansion panels.

31. An absorbent article, comprising:
   a garment having an absorbent structure, a longitudinal axis, a first waist region comprising an expansion panel having a wicking rate less than about 3 centimeters per 30 minutes, a second waist region, and a crotch region intermediate and interconnecting the first and second waist regions, the expansion panel forming an end flap that is disposed over and at least partially unadhered to the crotch region, the expansion panel adapted to elongate in a direction substantially perpendicular to the longitudinal axis; and
   a pair of separate elastomeric strap members each having opposite ends refastenably attached to the waist regions.

* * * * *